United States Patent
Tameishi et al.

(10) Patent No.: US 9,717,634 B2
(45) Date of Patent: Aug. 1, 2017

(54) METHOD AND APPARATUS FOR ROTATING AN ABSORBENT ARTICLE

(71) Applicant: The Procter & Gamble Company, Cincinnati, OH (US)

(72) Inventors: Kazuaki Tameishi, Akashi (JP); Michael Devin Long, Springfield Township, OH (US); David Carlton Ordway, Oxford, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/886,358

(22) Filed: Oct. 19, 2015

(65) Prior Publication Data
US 2016/0106596 A1     Apr. 21, 2016

Related U.S. Application Data

(60) Provisional application No. 62/066,420, filed on Oct. 21, 2014.

(51) Int. Cl.
*B65G 47/00* (2006.01)
*A61F 13/15* (2006.01)
(Continued)

(52) U.S. Cl.
CPC ...... *A61F 13/15764* (2013.01); *B65G 47/244* (2013.01); *B65G 47/848* (2013.01)

(58) Field of Classification Search
CPC ................ B65G 47/244; B65G 47/848; A61F 13/15764
(Continued)

(56) References Cited

U.S. PATENT DOCUMENTS

| 3,860,003 A | 1/1975 | Buell |
| 4,610,678 A | 9/1986 | Weisman et al. |

(Continued)

FOREIGN PATENT DOCUMENTS

| WO | WO 2008/155618 A2 | 12/2008 |
| WO | WO 2010/078572 A1 | 7/2010 |

OTHER PUBLICATIONS

PCT/US2015/056167 International Search Report dated Jan. 28, 2015, 12 pages.
(Continued)

*Primary Examiner* — William R Harp
(74) *Attorney, Agent, or Firm* — Sarah M. DeCristofaro

(57) ABSTRACT

An apparatus and method for rotating and transferring a discrete article. The rotation apparatus may include a slot portion defining a longitudinal slot axis. A head assembly may be positioned adjacent to the slot portion. The head assembly may include a transfer member. The transfer member may define a longitudinal transfer axis. A support member extending from the transfer member toward the slot portion may rotate about the longitudinal transfer axis. A first follower and a second follower may be operatively engaged with the support member. The first follower may include a first follower outer surface defining a first longitudinal follower axis and the second follower may include a second follower outer surface defining a second longitudinal follower axis. The first follower and the second follower may be positioned such that the first longitudinal follower axis and the second longitudinal follower axis intersect the longitudinal slot axis.

20 Claims, 19 Drawing Sheets

(51) Int. Cl.
*B65G 47/84* (2006.01)
*B65G 47/244* (2006.01)

(58) Field of Classification Search
USPC ........... 198/377.02, 377.04, 406, 411, 470.1, 198/471.1
See application file for complete search history.

(56) References Cited

U.S. PATENT DOCUMENTS

| | | | |
|---|---|---|---|
| 4,617,082 A * | 10/1986 | Oshefsky | A61F 13/15609 156/164 |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,025,910 A * | 6/1991 | Lasure | A61F 13/15764 198/377.04 |
| 5,447,219 A * | 9/1995 | Dworak | B65G 47/848 198/377.04 |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,916,661 A | 6/1999 | Benson et al. | |
| 6,107,539 A | 8/2000 | Palumbo et al. | |
| 6,545,197 B1 | 4/2003 | Muller et al. | |
| 6,722,494 B2 * | 4/2004 | Nakakado | A61F 13/15764 198/377.01 |
| 6,758,109 B2 | 7/2004 | Nakakado | |
| 6,790,798 B1 | 9/2004 | Suzuki et al. | |
| 7,569,039 B2 | 8/2009 | Matsuda et al. | |
| 7,770,712 B2 * | 8/2010 | McCabe | A61F 13/15764 198/463.1 |
| 8,011,493 B2 * | 9/2011 | Giuliani | B65G 47/244 198/406 |
| 8,607,959 B2 | 12/2013 | Papsdorf et al. | |
| 8,720,666 B2 | 5/2014 | Papsdorf et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2009/0312730 A1 | 12/2009 | LaVon et al. | |
| 2012/0061015 A1 | 3/2012 | LaVon et al. | |
| 2012/0061016 A1 | 3/2012 | LaVon et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | LaVon et al. | |
| 2013/0255865 A1 | 10/2013 | Brown et al. | |
| 2013/0270065 A1 | 10/2013 | Papsdorf et al. | |
| 2013/0270066 A1 | 10/2013 | Papsdorf et al. | |
| 2013/0270069 A1 | 10/2013 | Papsdorf et al. | |
| 2014/0112751 A1 | 4/2014 | Schneider et al. | |
| 2014/0113793 A1 | 4/2014 | Schneider et al. | |

OTHER PUBLICATIONS

PCT/US2015/025168 International Search Report dated Jan. 27, 2015, 7 pages.

* cited by examiner

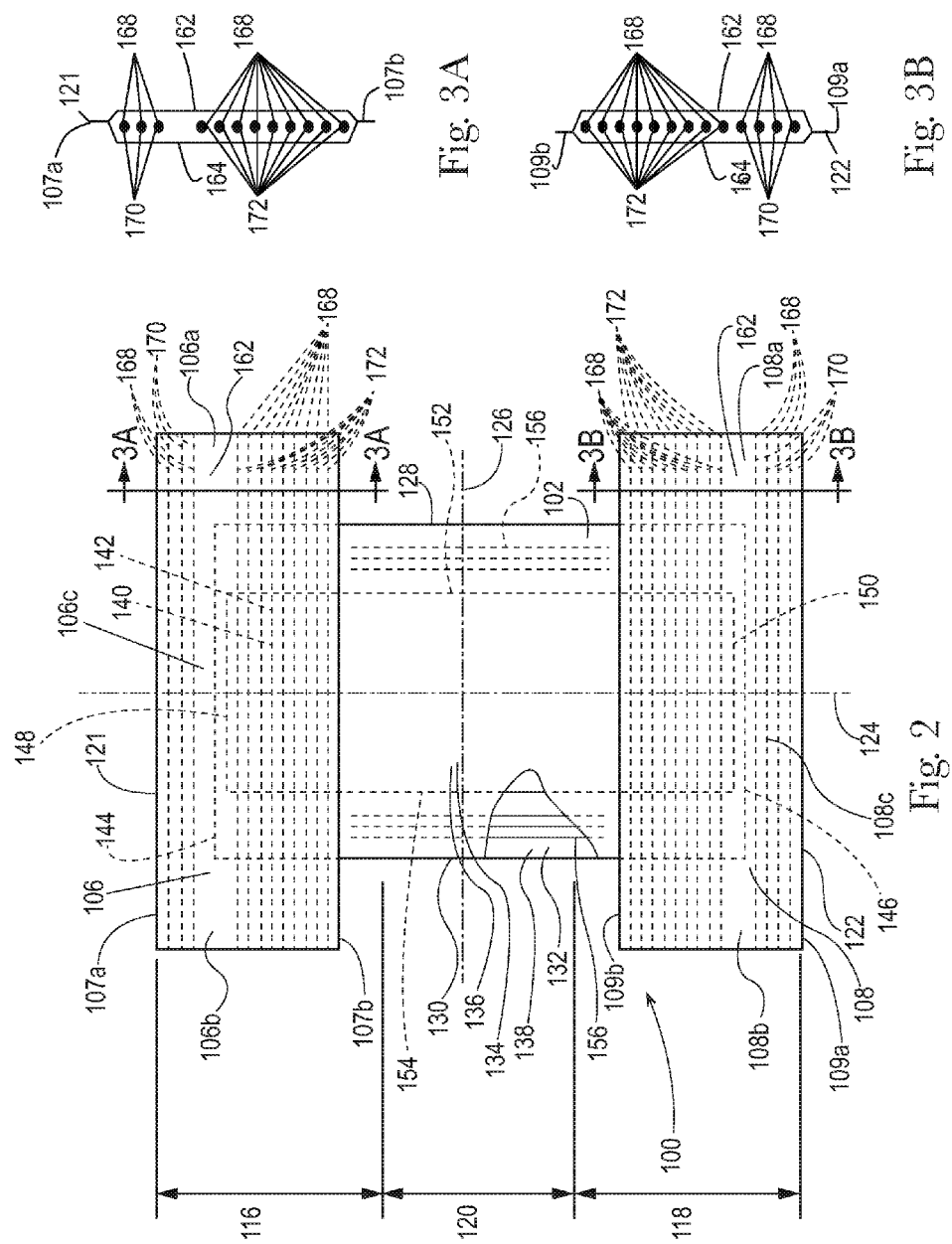

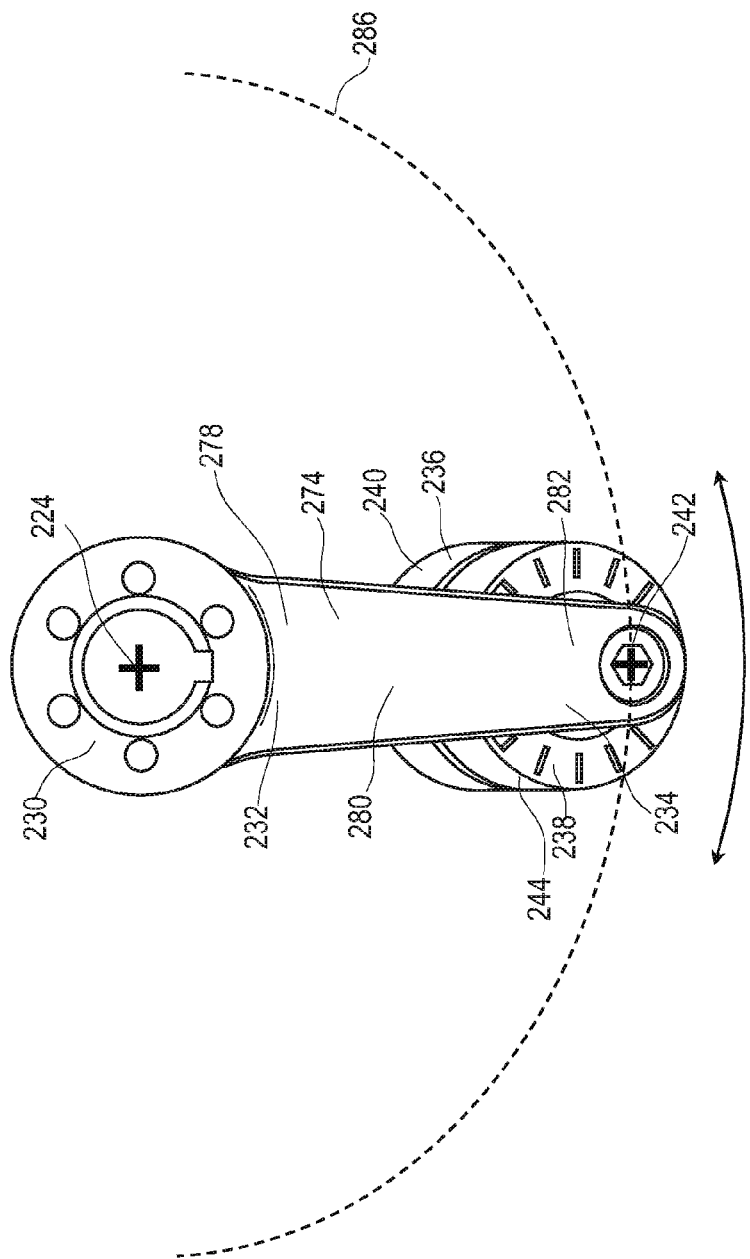

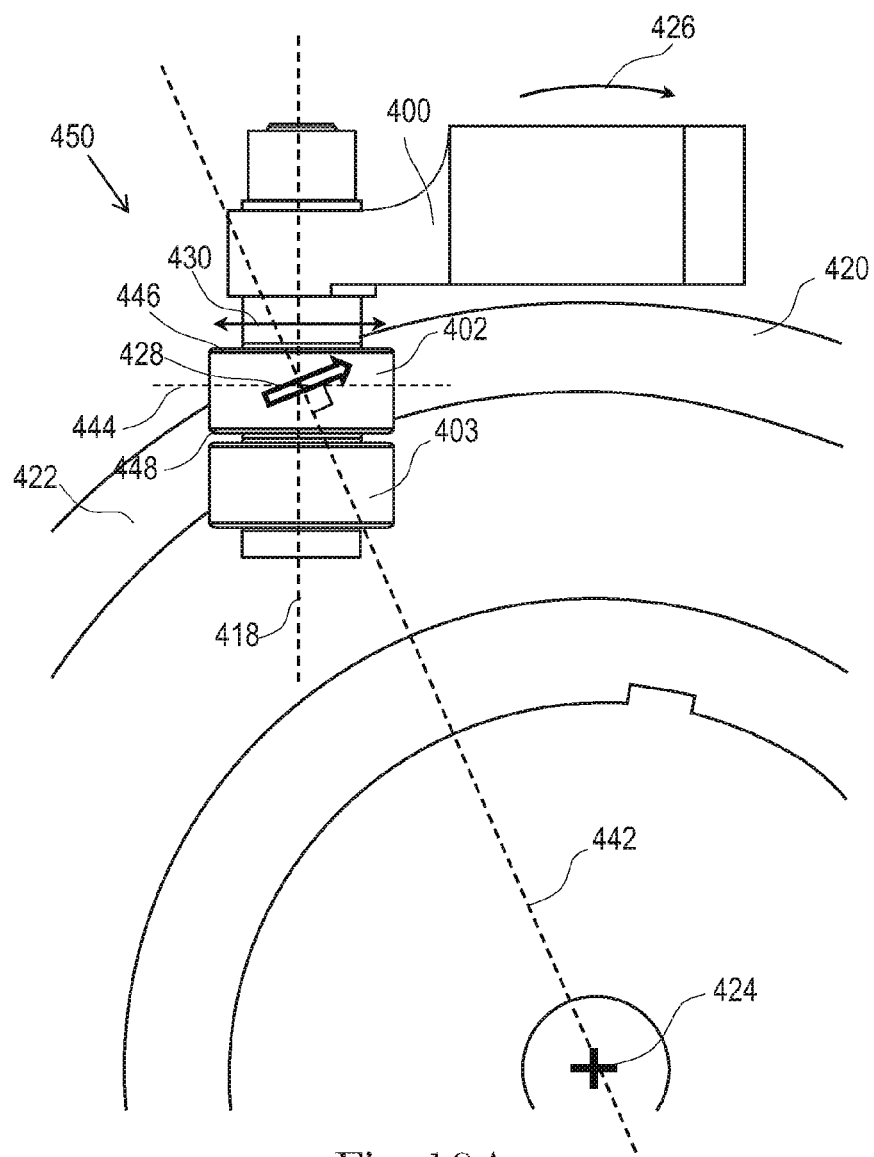
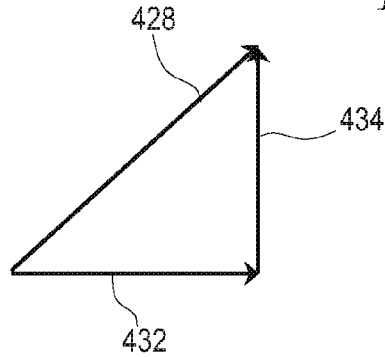
Fig. 10A
(Prior Art)
Fig. 10B

METHOD AND APPARATUS FOR ROTATING AN ABSORBENT ARTICLE

CROSS REFERENCE TO RELATED APPLICATION

This application claims the benefit of U.S. Provisional Application No. 62/066,420 filed on Oct. 21, 2014, the substance of which is incorporated herein by reference.

FIELD OF THE INVENTION

The present disclosure relates to methods and apparatuses for manufacturing absorbent articles, and more particularly, to methods and apparatuses for changing the orientation of an absorbent article.

BACKGROUND OF THE INVENTION

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from an advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete articles or other absorbent articles.

In some converting processes, the discrete chassis may be advanced in a machine direction MD and may be arranged with a longitudinal centerline parallel with the cross direction CD. Further, the discrete chassis may be positioned such that a lateral centerline of the discrete chassis is parallel with the machine direction. The discrete chassis may be joined to front and back waistbands to form a continuous length of absorbent articles. The continuous length of absorbent articles may then be folded in a cross direction CD. During the folding process in some converting configurations, one of the front and back waistband webs is folded 180° into a facing relationship with the opposing waistband. Stated another way, the front waist region may be folded into facing relationship with the back waist region.

In some processes, it may be necessary to rotate the folded, discrete absorbent article in order to change the orientation of the discrete absorbent article for downstream processing, such as packaging. Apparatuses and methods as disclosed in U.S. Publication No. 2014/00112751 have been developed to change the orientation of the discrete absorbent article. The apparatuses used to change the orientation of the discrete absorbent article may include the use of a cam device such as that disclosed in U.S. Pat. No. 6,758,109. A cam device may be used to translate linear motion into rotational motion. Current cam designs include a follower that engages one or more sidewalls of the cam device. Due to the interaction of the follower against the sidewalls of the cam device, the followers undergo both radial and axial forces. For example, the follower may experience sliding contact with the sidewall of the cam device and the sidewall of the cam may push the follower in one or more directions. Generally, these forces increase relative to the speed at which the follower moves about the cam device. Manufacturers have continued to increase the speed of processing equipment, including cam devices, to meet the demand for products.

The greater the radial and axial forces that act on the follower, the greater the wear on the follower. Followers that experience high radial and axial forces need to be replaced more frequently, and manufacturers are restricted in which materials may be used to make the followers. For example, followers may be required to be made from materials, such as metals, that can withstand these relatively high forces. Further, manufacturers have been required to use lubricants to help reduce the forces exerted on the followers. The use of lubricants may lead to an increase in manufacturing costs and contamination of the products being manufactured.

Therefore, it would be beneficial to provide a process and apparatus for rotating and transferring a discrete absorbent article such that the cam device may operate at relatively high speeds with a force reduction.

SUMMARY OF THE INVENTION

Aspects of the present disclosure relate to an apparatus and method for rotation and transferring a discrete article. In some embodiments, a rotation apparatus for rotating a discrete article may include a slot portion defined by a mounting surface. The slot portion may include a first slot surface, a second slot surface opposite the first slot surface, and an inner slot surface extending between the first slot surface and the second slot surface. The slot portion defines a longitudinal slot axis of rotation. The rotation apparatus may also include a head assembly positioned adjacent to the slot portion. The head assembly may include a transfer member having a proximal end portion and a distal end portion. The transfer member defines a longitudinal transfer axis of rotation. Further, at least a portion of the head assembly may be configured to rotate about the longitudinal transfer axis. A support member may extend from the transfer member toward the slot portion. The support member may have a proximal end portion and a distal end portion opposite the proximal end portion. The proximal end portion of the support member may be associated with the distal end portion of the transfer member. A first follower and a second follower may operatively engage with the distal end portion of the support member. The first follower may include a first follower outer surface and the second follower may include a second follower outer surface. The first follower outer surface and the second follower outer surface define a longitudinal follower axis, and the longitudinal follower axis intersects the longitudinal slot axis.

In some embodiments, a rotation apparatus for rotating a discrete article may include a slot portion defined by a mounting surface. The slot portion may include a first slot surface, a second slot surface opposite the first slot surface, and an inner slot surface extending between the first slot surface and the second slot surface. The slot portion may also include a motion zone and a dwell zone. The slot portion defines a longitudinal slot axis of rotation. The rotation apparatus may also include a transfer member positioned adjacent to the slot portion. The transfer member defines a longitudinal transfer axis of rotation, and includes a proximal end portion and a distal end portion. A support member may extend from the distal end portion of the transfer member toward the slot portion. The support member may have a proximal end portion and a distal end portion opposite the proximal end portion. A first follower and a second follower may operatively engage with the distal end portion of the support member. The first follower comprises a first follower outer surface and the second follower comprises a second follower outer surface. The first follower outer surface defines a first longitudinal follower axis and the second follower outer surface defines a second longitudinal follower axis. The first and second longitudinal follower axes intersects the longitudinal slot axis at the same point. Further, the transfer member and the support member may be configured to rotate about the longitudinal slot axis.

In some embodiments, A method of transferring and rotating discrete substrates may include the following steps: advancing a discrete substrate in a machine direction; providing a rotation apparatus comprising slot portion defined by a mounting surface, the slot portion comprising a first slot surface, a second slot surface opposite the first slot surface, and an inner slot surface extending between the first slot surface and the second slot surface, wherein the slot portion defines a longitudinal slot axis of rotation; rotating a head assembly about the longitudinal slot axis, wherein the head assembly is adjacent the slot portion, and wherein the head assembly comprises a transfer member defining a longitudinal transfer axis of rotation and a support member associated with a distal end portion of the transfer member; rotating the transfer member about a longitudinal transfer axis; rotating a support member about the longitudinal transfer axis, wherein the support member extends from the transfer member toward the slot portion; associating a first follower and a second follower with the slot portion, wherein the first follower and the second follower are operatively engaged with a distal end portion of the support member, wherein the first follower comprises a first follower outer surface and the second follower comprises a second follower outer surface, and wherein the first follower outer surface and the second follower outer surface are positioned to define a first longitudinal follower axis and a second longitudinal follower axis, respectively, and wherein the first longitudinal follower axis and the second longitudinal follower axis intersect the longitudinal slot axis; receiving the discrete substrate in a first position on at least a portion of the head assembly; and rotating the discrete substrate to a second position, wherein the first position is different than the second position.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A;

FIG. 3B is a cross-sectional view of the diaper pant of FIG. 2 taken along line 3B-3B;

FIG. 8 is a top view of a support member in accordance with one non-limiting embodiment of the present disclosure;

FIG. 10A is a schematic representation of a device;

FIG. 10B is a schematic representation of the forces acting on a follower of the device;

DETAILED DESCRIPTION OF THE INVENTION

Figure 1:
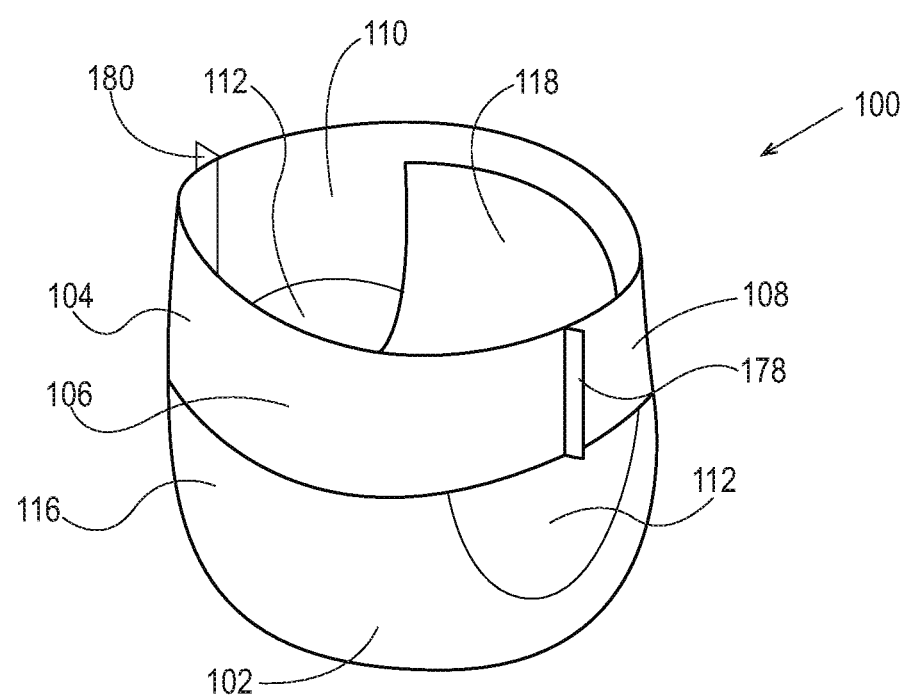
FIG. 1 is a perspective view of a diaper pant.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (for example, they are intended to be discarded after a single use and may also be configured to be recycled, composted or otherwise disposed of in an environmentally compatible manner).

"Joined" is used herein to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral.""Substrate" is used herein to describe a material which is primarily two-dimensional (i.e. in an XY plane) and whose thickness (in a Z direction) is relatively small (i.e. $\frac{1}{10}$ or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (for example, seams, heat bonds, pressure welds, adhesives, cohesive bonds, mechanical fasteners, etc.). A pant can be preformed anywhere along the circumference of the article in the waist region (for example, side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be pre-formed by various techniques including, but not limited to, joining together portions of the diaper using refastenable and/or permanent closure members (for example, seams, heat bonds, pressure welds, adhesives, cohesive bonds, mechanical fasteners, etc.). In addition, pant diapers can be preformed anywhere along the circumference of the waist region (for example, side fastened or connected, front waist fastened or connected, rear waist fastened or connected).

The present disclosure relates to methods and apparatuses for changing the orientation of discrete absorbent articles advancing in a machine direction. The methods and apparatuses discussed herein operate to rotate and transfer the discrete article from a first carrier apparatus to a second carrier apparatus. The discrete article may advance in a first orientation on the first carrier apparatus and may be rotated and shifted to a second orientation and advanced onto the second carrier apparatus using the methods and apparatuses disclosed herein. In the first orientation, the longitudinal centerline of the discrete article may extend in a cross direction. The rotation apparatus operates to rotate the discrete article to a second orientation where the longitudinal centerline of the discrete article extends in the machine direction. However, it is to be appreciated that the discrete absorbent article may be arranged in various configurations depending upon the desired orientation for downstream processing.

The rotation apparatus may include a slot portion defined by a mounting surface and a head assembly operatively engaged with the slot portion. The slot portion may define a longitudinal slot axis of rotation. The head assembly may be configured to rotate about the longitudinal slot axis of rotation. The head assembly may include a transfer member and a support member. The transfer member and the support member may rotate about a longitudinal transfer axis causing a portion of the head assembly to rotate. The support member may extend from the transfer member toward the slot portion. The support member may be operatively engaged with a first follower and a second follower. The first follower and the second follower may associate with the slot portion causing the transfer member to rotate about the longitudinal transfer axis. During rotation of the head assembly about the longitudinal slot axis and the transfer member about the longitudinal transfer axis, the first longitudinal follower axis and the second longitudinal follower axis intersect the longitudinal slot axis.

The position of the first follower, which defines the first longitudinal follower axis, and the second follower, which defines the second longitudinal follower axis, results in a reduction of both the axial force that may be exerted on each follower as the head assembly rotates about the longitudinal slot axis. This reduction in force allows manufacturers, for example, to operate such apparatuses for relatively longer periods of time without having to replace worn parts and/or to use a relatively greater assortment of materials, such as polymers, to make the followers.

While the present disclosure relates to discrete absorbent articles that may be folded, rotated, and transferred, it is to be appreciated that the methods and apparatuses described herein may be used to change the orientation of various discrete articles arranged in various configurations. For example, the discrete article may include a fully assembled absorbent article, or the discrete article may include one or more components of an absorbent article. In some exemplary configurations, the discrete article may include a discrete chassis having a topsheet, backsheet, and an absorbent core. The discrete article may be folded, or may be configured in a flat, contracted or uncontracted state. The transfer apparatus may be used to rotate and transfer a discrete article in various configurations and orientations.

The processes and apparatuses discussed herein may be used to rotate various types of discrete articles, some of which may be used in the manufacture of different types of absorbent articles. To help provide additional context to the subsequent discussion, the following provides a general description of absorbent articles in the form of diaper pants that may be rotated and shifted in accordance with the methods and apparatuses disclosed herein. While the present disclosure relates to diaper pants, it is to be appreciated that the methods and apparatuses disclosed herein may be used in the manufacture of various types of absorbent articles.

FIGS. 1 and 2 show an example of a diaper pant 100 that may be transferred and/or rotated with the apparatuses and methods disclosed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wetlaid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730 A1; and U.S. Patent Publication No. 2013/0255865 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to transfer and/or rotate discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. US2005/0107764 A1, US2012/0061016 A1, and US2012/0061015 A1; 2013/0255861 A1; 2013/0255862 A1; 2013/0255863 A1; 2013/0255864 A1; and 2013/0255865 A1.

Figure 4:
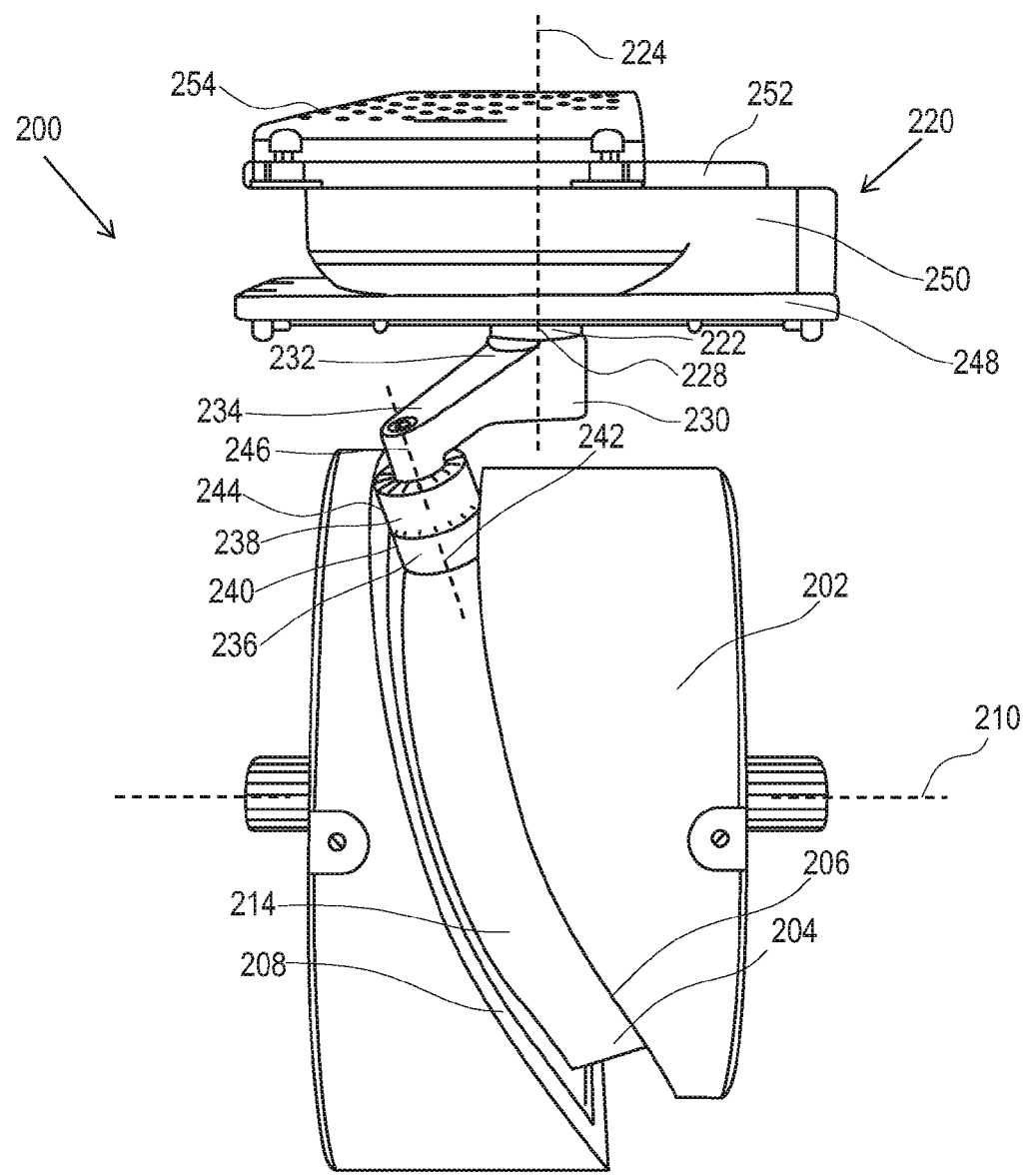
FIG. 4 is a front view of a rotation apparatus in accordance with one non-limiting embodiment of the present disclosure.

FIG. 4 illustrates a rotation apparatus 200 that may be used to transfer and rotate a discrete absorbent article 100, or portion thereof. The rotation apparatus 200 may include a slot portion 204 and a head assembly 220 positioned adjacent to the slot portion 204. The slot portion 204 may extend in a continuous, substantially circular path and define a longitudinal slot axis 210. The slot portion 204 may be defined by a mounting surface 202. The slot portion 204 may substantially surround the mounting surface 202. The slot portion 204 may include a first slot surface 206 and a second slot surface 208, which is opposite the first slot surface 206.

Figure 6:
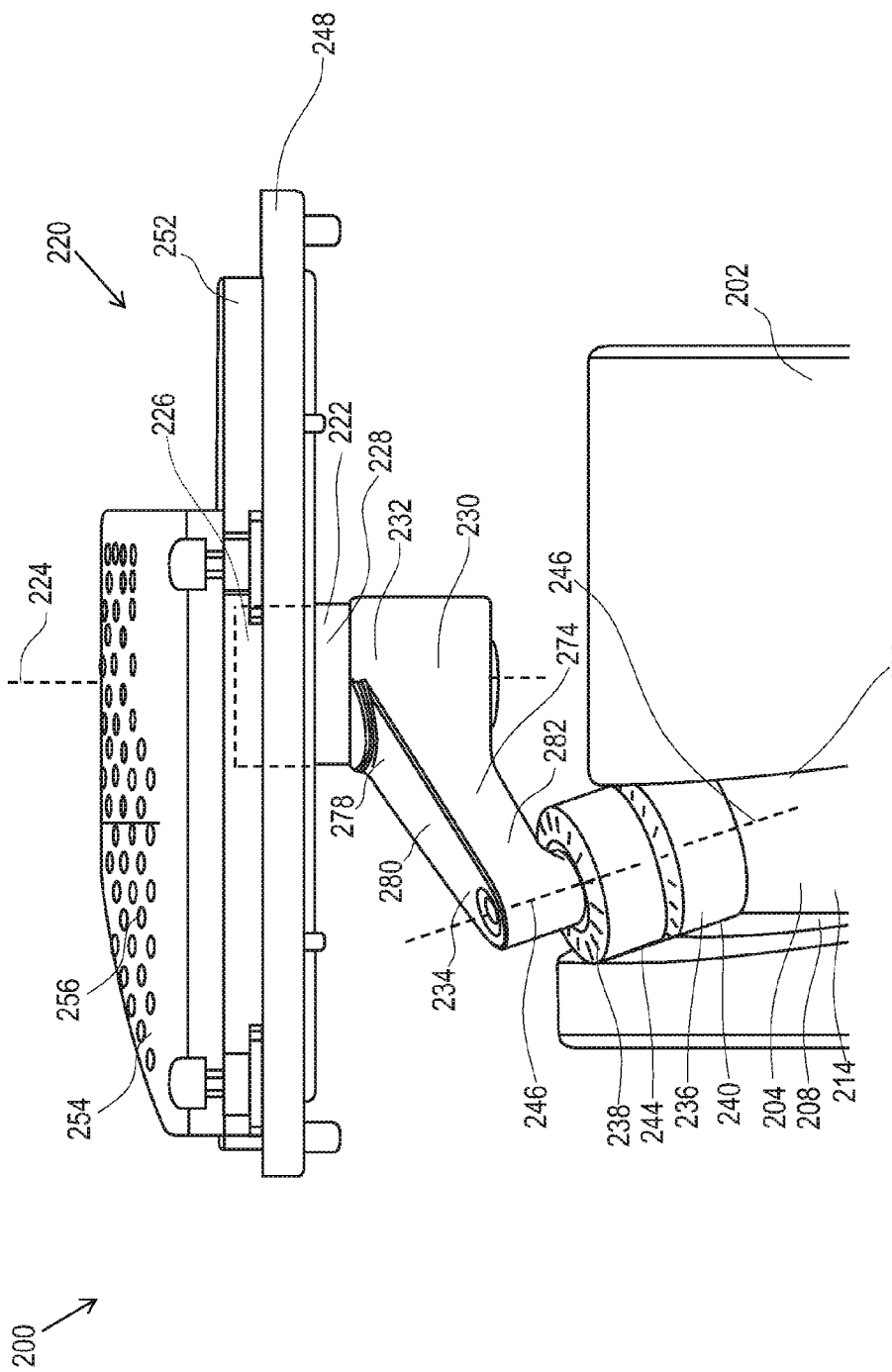
FIG. 6 is a partial front view of a rotation apparatus in accordance with one non-limiting embodiment of the present disclosure.

As previously stated, the rotation apparatus 200 may also include a head assembly 220 positioned adjacent to the slot portion 204. The head assembly 220 may include a transfer member 222. The transfer member 222 may be a cylindrical member that defines a longitudinal transfer axis 224 of rotation. The transfer member 22 may be configured to rotate about the longitudinal transfer axis 224. The transfer member 222 may include a proximal end portion 226 (as shown in FIG. 6) positioned away from the slot portion 204 and a distal end portion 228, opposite the proximal end portion 226. A support member 230 may extend from the distal end portion 228 of the transfer member 222 toward the slot portion 204. The support member 230 may include a proximal end portion 232 and a distal end portion 234. The proximal end portion 232 of the support member 230 may be operatively associated with the transfer member 222. More specifically, the proximal end portion 232 of the support member 230 may rotate with the transfer member 222 about the longitudinal transfer axis 224. The distal end portion 234 of the support member 230 may be adapted to receive a first follower 236 and a second follower 238.

The first follower 236 and the second follower 238 each may be operatively engaged with the distal end portion 234 of the support member 230 so that each of the first follower 236 and the second follower 238 may rotate. More specifically, the first follower 236 may include a first follower outer surface 240 that rotates about a first longitudinal follower axis 242. The second follower 238 may include a second follower outer surface 244 that rotates about a second longitudinal follower axis 246. The first longitudinal follower axis 242 may be parallel with the second longitudinal follower axis 246. Further, the first longitudinal follower axis 242 and the second longitudinal follower axis 246 may intersect the longitudinal slot axis 210. The position of the first longitudinal follower axis 242 and the second longitudinal follower axis 246 may aid in the reduction of the force exerted on the first follower 236 and the second follower 238. The reduction in force will be discussed in more detail herein.

In some embodiments, the first longitudinal follower axis 242 and the second longitudinal follower axis 246 may be in line with one another. Thus, the first longitudinal follower axis 242 and the second longitudinal follower axis 246 may intersect the longitudinal slot axis at the same location. In some embodiments, the first longitudinal follower axis 242 and the second longitudinal follower axis 246 may not be in line with one another. Thus, the first longitudinal follower axis 242 and the second longitudinal follower axis 246 may intersect the longitudinal slot axis at the different locations.

As the head assembly 220 rotates about the longitudinal slot axis 210, the first follower 236 may engage the first slot surface 206 and the second follower 238 may engage the second slot surface 208. The first slot surface 206 may be designed to impart a desired motion profile of the head assembly 220. More specifically, the first slot surface 206 may be designed such that when the first follower 236 engages the first slot surface 206, the support member 230 and the transfer member 222 rotate about the longitudinal transfer axis 224 in a desired motion profile. The second slot surface 208 may be designed in view of the first slot surface 206 and the geometry of the support member 230. It is to be appreciated that the first follower 236 and the second follower 238 may be in fixed relationship to one another due to the geometry, or the structure, of the support member 230. The change in the slot portion 204 as the head assembly 220 rotates about the longitudinal slot axis 210 may cause the support member 230 and the transfer member 222 to rotate in a desired motion profile about the longitudinal transfer axis 224.

It is to be appreciated that the second slot surface 208 may be designed such that when the second follower 238 engages the second slot surface 206, the support member 230 and the transfer member 222 rotate about the longitudinal transfer axis 224 in a desired motion profile. The first slot surface 206 may be designed in view of the second slot surface 208 and/or the geometry of the support member 230.

Still referring to FIG. 4, the head assembly 220 may also include a connection member 248 associated with the transfer member 222. The connection member 248 may be associated with the transfer member 222 such that the transfer member 222 may rotate about the longitudinal transfer axis 224 while the connection member 248 may remain stationary. Stated another way, the connection member 248 may not rotate about the longitudinal transfer axis 224. In some embodiments, a bearing (not shown) may be used to associate the connection member 248 and the transfer member 222. The connection member 248 may be attached to a frame 328, as illustrated and discussed with reference to FIG. 14.

As illustrated in FIG. 4, the head assembly 220 may also include a brace member 250 associated with the transfer member 222. The brace member 250 may remain stationary as the transfer member 222 rotates about the longitudinal transfer axis 224. The brace member 250 may also be associated with the connection member 248. In some embodiments, a bearing (not shown) may be used to associate the brace member 250 and the transfer member 222. The brace member 250 may be supported by the connection member 248. Further, the brace member 250 may be used to control the amount of vacuum and/or pressure, which may aid in holding the discrete article on the head assembly 220 and/or in removing the discrete article from the head assembly 220. Stated another way, the brace member 250 may be used to control a flow of gas that aids in holding the discrete article on the head assembly and/or in removing the discrete article from the head assembly. Thus, the brace member 250 may be any shape that allows for the control of vacuum and/or pressure on the discrete article. It is to be appreciated that the brace member 250 is not necessary and the discrete substrate may be held onto the head assembly 220 by other means such as with adhesive or mechanical devices, such as clips or rotatable arms.

Further, the head assembly, 220 may include a rotation member 252 associated with the transfer member 222. The rotation member 252 may be fixedly attached with the transfer member 222 such that the rotation member 252 rotates with the transfer member 222 about the longitudinal transfer axis 224. The rotation member 252 may be a semi-circular shape, as shown in FIG. 4, or any other shape that allows the discrete article to be rotated about the longitudinal transfer axis 224. The rotation member 252 may be adapted to receive the discrete article. Thus, the rotation member 252 may be in fluid communication with the brace member 250. As the discrete article is received onto the rotation member 252, vacuum and/or pressure may be applied to the discrete article.

However, in some embodiments, the rotational member 252 may be associated with a receiving member 254. The receiving member 254 may be fixedly attached to the rotational member 252 and/or the transfer member 222. The receiving member 254 may be configured to rotate about the longitudinal transfer axis 224. The receiving member 245 may be shaped to accept one or more discrete articles. In some embodiments, the receiving member 254 may include one or more apertures 256, as shown in FIG. 4, which may be in fluid communication with the brace member 250. The one or more apertures 256 may be used, for example, to apply vacuum to or pressure to the absorbent article. In some embodiments, the receiving member 245 may be in fluid communication with a fluid handling device that supplies vacuum and/or pressure through the use/control of a gas.

In summary, the mounting surface 202 and the slot portion 204, which defines a longitudinal slot axis 210 of rotation, may remain stationary during operation of the rotation apparatus 200. The head assembly 220 may rotate about the longitudinal slot axis 210 of rotation. As the head assembly 220 progresses around the longitudinal slot axis 210 the first follower 236 and the second follower 238 engage the slot portion 204, which may extend in a circular path about the longitudinal slot axis 210. The profile of the slot portion 204 causes at least one of the first follower 236 and the second follower 238 to engage the first slot surface 206 and the second slot surface 208, respectively. The engagement of the followers 236, 238 with the slot portion 204 may result in the rotation of the transfer member 222 and the support member 230 about the longitudinal transfer axis 224. Further, the rotation member 252, which may include a receiving member 254, may rotate with the transfer member 222 and the support member 230 about the longitudinal transfer axis 224. As previously stated, the discrete article may be received by the receiving member and/or the rotation member 252. The discrete article may then be rotated by the rotation member 252, which will be described in more detail herein.

Figure 5:
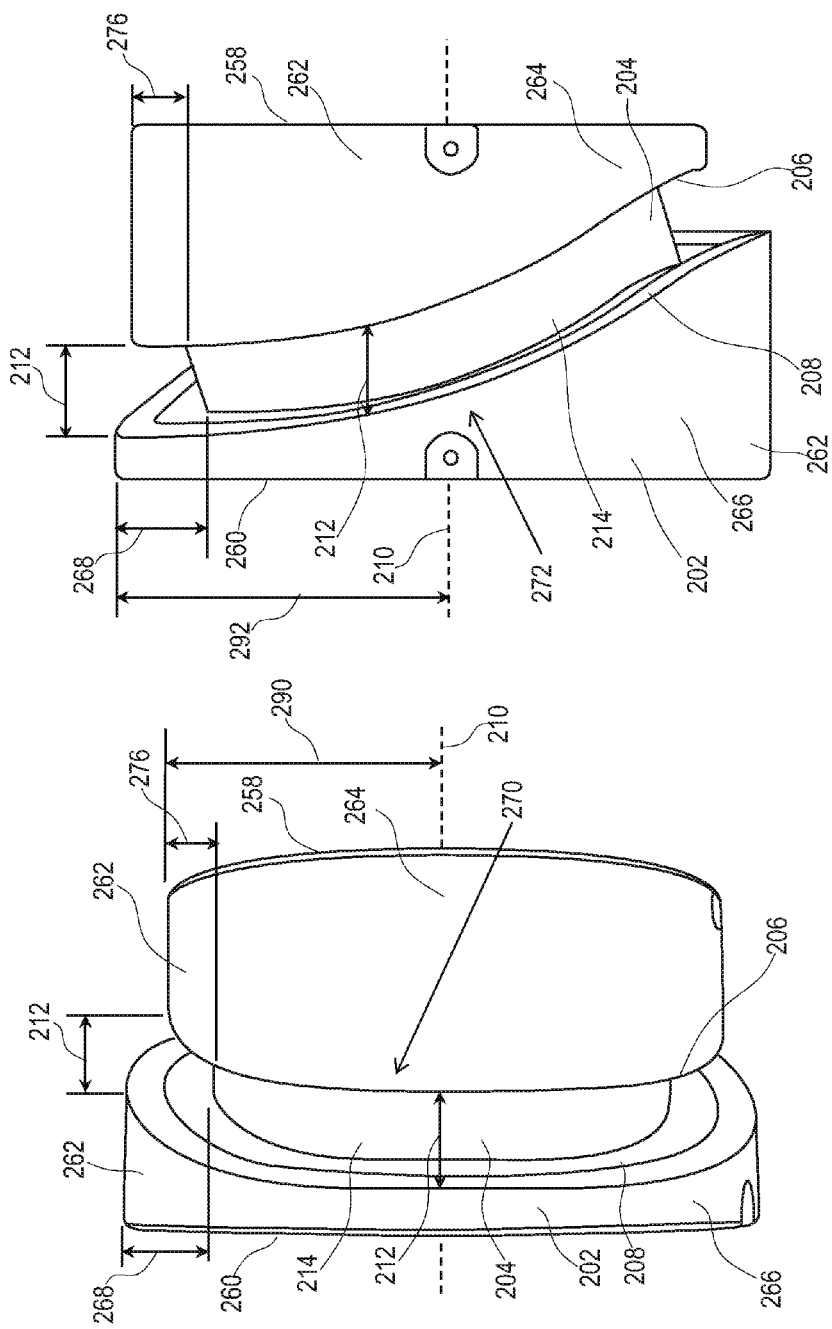
FIG. 5A is a front view of a slot portion extending radially outward from a mounting surface in accordance with one non-limiting embodiment of the present disclosure.
FIG. 5B is a front view of a slot portion extending radially outward from a mounting surface in accordance with one non-limiting embodiment of the present disclosure.

Referring to FIGS. 5A and 5B, the slot portion 204 may extend in a continuous, circular path about a longitudinal slot axis 210 of rotation. Further, the slot portion 204 may be defined by a mounting surface 202. The mounting surface 202 may be any surface that supports the slot portion 204 and/or about which the slot portion may substantially surround. In some embodiments, the mounting surface 202 may include a first face 258 and a second face 260 opposite the first face 258. An outer mounting surface 262 may extend between the first face 258 and the second face 260. The slot portion 204 may extend around the outer mounting surface 262 and may separate the outer mounting surface 262 into a first mounting portion 264 and a second mounting portion 266.

In some embodiments, the first mounting portion 264 and the second mounting portion 266 may be perpendicular to the first face 258 and the second face 260, respectively, as illustrated in FIGS. 5A and 5B. Stated another way, the mounting surface 202 may also be designed such that the first mounting portion 264 and/or the second mounting portion 266 are substantially parallel to the longitudinal slot axis 210. However, the first mounting portion 264 and the second mounting portion 266 may each slope from the slot portion 204 to the first face 258 and the second face 260, respectively. The slope may be a downward slope. It is to be appreciated that the slope may also be an upward slope. For example, the first mounting portion 264 and the second mounting portion 266 may slope from the first face 258 and the second face 260, respectively, toward the slot portion 204. The slope may also vary from an upward slope to a downward slope around the mounting surface 202. Further, it is to be appreciated that in some embodiments, the mounting surface 202 may not include a first face 258 and a second face 260.

The slot portion 204 may be defined by the mounting surface 202. More specifically, the slot portion 204 may include a first slot height 276 and a second slot height 268. The slot height may be the vertical distance between the portion of the slot portion that intersects the inner slot surface 214 to the most radially outward portion of the mounting surface. The first slot height 276 may be the vertical distance between the portion of the slot portion that intersects the inner slot surface 214 adjacent the first slot surface 206 to the most radially outward portion of the first mounting portion 264. The second slot height 268 may be the vertical distance between the portion of the slot portion that intersects the inner slot surface 214 adjacent the second slot surface 208 to the most radially outward portion of the second mounting portion 266. The slot height 268 may be such that the followers 236, 238 are able to rotate about their first and second longitudinal follower axes 242, 246 without being inhibited by the mounting surface 202. The slot height 268 may be non-uniform or uniform as the slot portion 204 extends around the mounting surface 202.

Each of the first mounting portion 264 and the second mounting portion 266 may have a first radius 290 and a second radius 292, respectively. The first radius 290 may be measured perpendicularly from the longitudinal slot axis 210 to the outer mounting surface 262 of the first mounting portion 264. The second radius 292 may be measured perpendicularly from the longitudinal slot axis 210 to the outer mounting surface 262 of the second mounting portion 266. The first radius 290 and the second radius 292 may be non-uniform or uniform about the outer mounting surface 262. The first radius 290 may be greater than, less than, or equal to the second radius 292. The difference in the first radius 290 and the second radius 292 may be, in part, due to the configuration of the first follower and the second follower. For example, the first radius 290 may be less than the second radius 292 such that the first slot surface only high enough to engage the first follower 236. The second radius 292 may be greater than the first radius 290 such that the second slot surface is high enough to engage the second follower 238.

The slot portion 204 may include a dwell zone 270 as illustrated in FIG. 5A and a motion zone 272 as illustrated in FIG. 5B. The dwell zone may be any portion of the slot portion 204 that allows the head assembly 220, as shown in FIG. 4, to rotate about the longitudinal slot axis 210 while the transfer member 222, support member 230, and the rotation member 248 fail to rotate or remain stationary with respect to the longitudinal transfer axis 224. In some embodiments, for example, the dwell zone 270 may include a substantially linear slot portion 202. The substantially linear slot portion 202 may extend in a direction substantially perpendicular to the longitudinal slot axis 210. Further, the dwell zone 270 may include a slot portion 202 wherein the first slot surface 206 and the second slot surface 208 are at an angle to the longitudinal slot axis 210. For example, the first slot surface 206 may be at an obtuse angle with respect to the longitudinal slot axis 210 and the second slot surface 208 may be at an acute angle with respect to the longitudinal slot axis 210, or vice versa. Stated another way, the first slot surface 206 and the second slot surface 208 may be positioned such that either the first slot surface 206 engages the first follower outer surface 240 or the second slot surface 208 engages the second follower outer surface 244. It is to be appreciated that a dwell zone 270 may not include a substantially linear slot portion. A dwell zone may be any portion of the slot portion that does not result in the head assembly rotating about the longitudinal transfer axis 224.

As previously stated, the slot portion 204 may include a motion zone 272. The motion zone 272 is any portion of the slot portion 204 that allows the head assembly 220, as shown in FIG. 4, to rotate about the longitudinal slot axis 210 while the transfer member 222, support member 230, and the rotation member 248 rotate about the longitudinal transfer axis 224. In the motion zone 272, a portion of the head assembly 220 rotates about the longitudinal transfer axis 224. In some embodiments, for example, the motion zone 272 may include a substantially curvilinear slot portion 204. The curvilinear slot portion 204 may be at an angle to the longitudinal slot axis 210. Stated another way, the curvilinear slot portion 202 may extend from a position adjacent the second face 260 toward a position adjacent the first face 258 or vice versa. Further, the motion zone 272 may include a slot portion 202 wherein the first slot surface 206 and the second slot surface 208 are at an angle to the longitudinal slot axis 210. For example, the first slot surface 206 may be at an obtuse angle with respect to the longitudinal slot axis 210 and the second slot surface 208 may be at an acute angle with respect to the longitudinal slot axis 210. Stated another way, the first slot surface 206 and the second slot surface 208 may be positioned such that either the first slot surface 206 engages the first follower outer surface 240 or the second slot surface 208 engages the second follower outer surface 244. The motion portion 272 may also include a portion of the slot portion 202 where the first slot surface 206 and the second slot surface 208 are substantially perpendicular to the longitudinal slot axis 210.

The motion zone 272 may result in the rotation member 252 rotating in a clockwise or counterclockwise motion about the longitudinal transfer axis 224. In the motion zone 272, when the first slot surface 206 engages the first follower outer surface 240, the first follower 236 may be moved toward the second face 260 and the rotation member 252 may be rotated in the same direction as the first follower 236. Thus, the rotation member 252 may rotate about the longitudinal transfer axis 224 in a clockwise motion. Similarly, in the motion zone 272, when the second slot surface 208 engages the second follower outer surface 244, the second follower 238 may be moved toward the first face 258 and the rotation member 252 may be rotated in the same direction as the second follower 238. Thus, the rotation member 252 may rotate about the longitudinal transfer axis 224 in a counterclockwise motion.

It is to be appreciated that the slot portion 204 may be manufactured with any number of dwell zones 270 and motion zones 272. For example, the slot portion 204 may include two dwell zones and two motion zones during one full revolution of the head assembly about the longitudinal slot axis. It is also to be appreciated that the slot portion 204 may be manufactured without a dwell zone 270.

Still referring to FIGS. 5A and 5B, the slot portion 204 may also include a slot width 212. The slot width 212 may be the distance between the first slot surface 206 and the second slot surface 208 measured parallel to the longitudinal slot axis 210. The slot width 212 may be uniform or non-uniform as the slot portion 204 extends about the mounting surface 202. The slot width 212 may be determined in view of the geometry, or structure, of the support member 230 and the geometry, or structure, of the first and second followers 236, 238. The slot width 212 may be such that only one of the first follower or the second follower engages the slot portion at a point in time. Stated another way, the rid width 212 may be determined such that the first follower and the second follower do not simultaneously engage the slot portion 204 as the head assembly rotates about the longitudinal slot axis and a portion of the head assembly rotates about the longitudinal transfer axis 224. In some embodiments, it is to be appreciated that the first follower and the second follower may contact the first slot surface and the second slot surface simultaneously.

FIG. 6 illustrates a partial, end view of the rotation apparatus 200. As previously discussed, the rotation apparatus 200 may include a head assembly 220 positioned adjacent to a slot portion 204. In some embodiments, the head assembly 220 may include a receiving member 254 associated with a rotation member 252, which are each configured to rotate about the longitudinal transfer axis 224 and are moveably associated with the transfer member 222. The head assembly 220 may also include a connection member 248 that is associated with the transfer member 222 and may be configured to remain stationary as the transfer member 222 rotates about the longitudinal transfer axis 224. Further, the head assembly may also include a transfer member 222 having a distal end portion 228 and a proximal end portion 226 and a support member 230 associated with the distal end portion 228.

The support member 230 may include a distal end portion 234 and a proximal end portion 232. The proximal end portion 232 of the support member 230 may be associated with the distal end portion 228 of the transfer member 222. More specifically, the proximal end portion 232 of the support member 230 may be fixedly associated with adhesive or other mechanical device, such as a screw, clamp, or nail to the transfer member 222. The support member 230 may be associated with the transfer member 222 such that the support member 230 rotates with the transfer member 222 about the longitudinal transfer axis 224.

In some embodiments, such as that illustrated in FIG. 6, the support member 230 may include a first arm 274. The first arm 274 may include a first end portion 278, a second end portion 282 opposite the first end portion 278, and an intermediate portion 280 between the first end portion 278 and the second end portion 282. In some embodiments, the first end portion 278 of the first arm 274 may be associated with the transfer member 222. The second end portion 282 of the first arm 274 may be configured to operatively engage with the first follower 236 and the second follower 238. The first follower 236 and the second follower 238 may be moveably attached to the second end portion 282. Thus, the first follower 236 may rotate about the first longitudinal follower axis 242 and the second follower 238 may rotate about the second longitudinal follower axis 246.

It is to be appreciated that the support member 230 may include any number of arms that associate with the followers. For example, the support member 230 may include a first arm and a second arm. The first follower may be associated with the first arm and the second follower may be associated with the second arm. The first arm and the second arm may be configured such that the first follower engages the first slot surface and the second follower engages the second slot surface. The support member 230 may have any configuration that results in the followers engaging the appropriate surfaces of the slot and the transfer member rotating about the longitudinal transfer axis in the desired motion.

Figure 7:
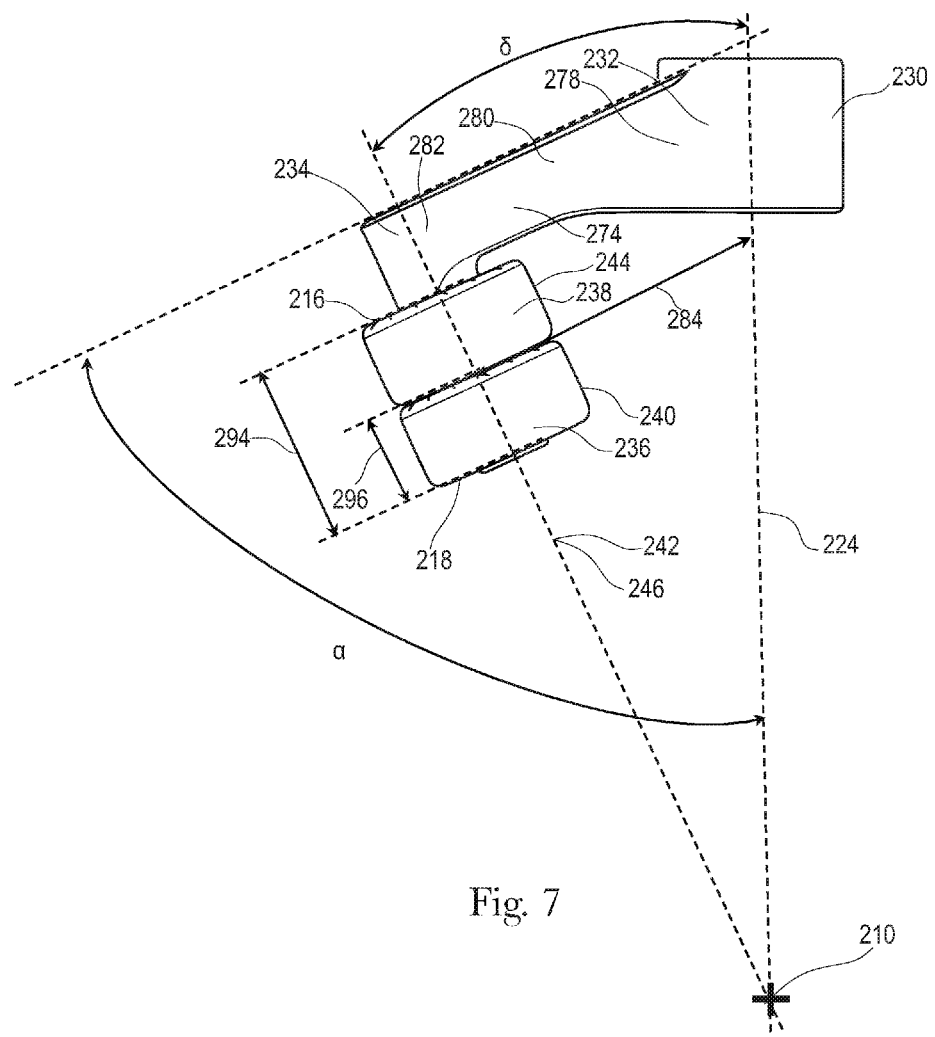
FIG. 7 is a side view of a support member in accordance with one non-limiting embodiment of the present disclosure.

As illustrated in FIG. 7, the support arm 230 may include a follower height 294. The follower height 294 is the distance taken parallel to the first follower outer surface 240 and the second follower outer surface 244 between the top 216 of the second follower and the bottom 218 of the first follower. The support member 230 may also include a follower midpoint axis 296. The follower midpoint axis 296 may be positioned between the top 216 second follower 238 and the bottom 218 of the first follower 236, or positioned at a distance of half of the follower height 294 measured parallel to the first follower outer surface 240 from either the top 216 or the bottom 218 of the first follower 236. The follower midpoint axis 296 may be perpendicular to the first longitudinal follower axis 242 and/or the second longitudinal follower axis 246.

In some embodiments, the first follower and the second follower may not be positioned such that the first longitudinal follower axis and the second longitudinal follower axis are in line with one another, or, stated another way, positioned on top of one another. Thus, the first follower may have a follower midpoint axis and the second follower may have a follower midpoint axis. Similarly, each of the first follower and the second follower may have an independent follower height.

The first arm 274 may include a first arm length 284. The first arm length 284 may be the distance measured from the intersection of the follower midpoint axis 296 and the first longitudinal follower axis 242 in a direction parallel to the follower midpoint axis 296 to the longitudinal transfer axis 224. The first arm length 284 may be determined, in part, based on the clearance needed between the transfer member 222 and/or the support member 230 and the slot portion 204. In some embodiments, the first arm length 284 may be from about 30 mm to about 400 mm and/or from about 50 mm to about 250 mm and/or from about 75 mm to about 175 mm and/or from about 115 mm to about 130 mm, including all 0.1 mm increments therebetween. It is to be appreciated that the arm length may be any length that aids in the reduction of force exerted on the follower, which will be descried in more detail herein.

Still referring to FIG. 7, the first arm 274 may extend from the transfer member 222 toward the slot portion 204. The first arm 274 may extend toward the slot portion 204 forming a first vertical arm angle α with the longitudinal transfer axis 224. The first follower 236 may be positioned perpendicular to the first vertical arm angle α. More specifically, the first follower 236 may be operatively connected to the transfer member 222 and may include a first follower outer surface 240 that substantially surrounds a first longitudinal follower axis 242. The first longitudinal follower axis 242 may be perpendicular to the first arm 274, which is positioned at a first vertical arm angle α. The first vertical arm angle α may be such that the first longitudinal follower axis 242 and the second longitudinal follower axis 246 intersect the longitudinal slot axis 210, as illustrated in FIG. 4.

However, it is to be appreciated that in some embodiments, the first arm 274 may not be positioned perpendicular to the first longitudinal follower axis 242. Independent of the position of the first arm 274, the first longitudinal follower axis may form a first follower angle δ with the longitudinal transfer axis 224. The first follower angle δ may be such that the first longitudinal follower axis 242 intersects the longitudinal slot axis 210.

Similarly, the second longitudinal follower axis 246 may form a second follower angle with the longitudinal transfer axis 224, not shown. The second follower angle may be such that the second longitudinal follower axis intersects the longitudinal slot axis 210. The first follower angle δ and the second follower angle (not shown) may be from about 5 degrees to about 60 degrees and/or from about 10 degrees to about 45 degrees and/or from about 20 degrees to about 30 degrees, including all 0.1 increments therebetween. For example, 45.6 degrees may be included in the aforementioned range. The first follower angle may be greater than, less than, or equal to the second follower angle.

It is to be appreciated that the longitudinal transfer axis 224 may not intersect the longitudinal slot axis 210. Thus, in some embodiments, the first follower angle δ and the second follower angle may be measured from an axis extending perpendicular to the longitudinal slot axis 210 to each of the first longitudinal follower axis 242 and the second longitudinal follower axis 244.

It is also to be appreciated that positioning the first arm 274 so that the first and second longitudinal follower axes 242, 246 intersect the longitudinal slot axis 210, or positioning the followers 236, 238 such that the first and second longitudinal follower axis 242, 246 are at a first and second follower angle δ, which results in the first and second longitudinal follower axis 242, 246 intersecting the longitudinal slot axis 210, may result in a reduction of forces, radial and axial, exerted on the first and second followers 236, 238.

Figure 9A:
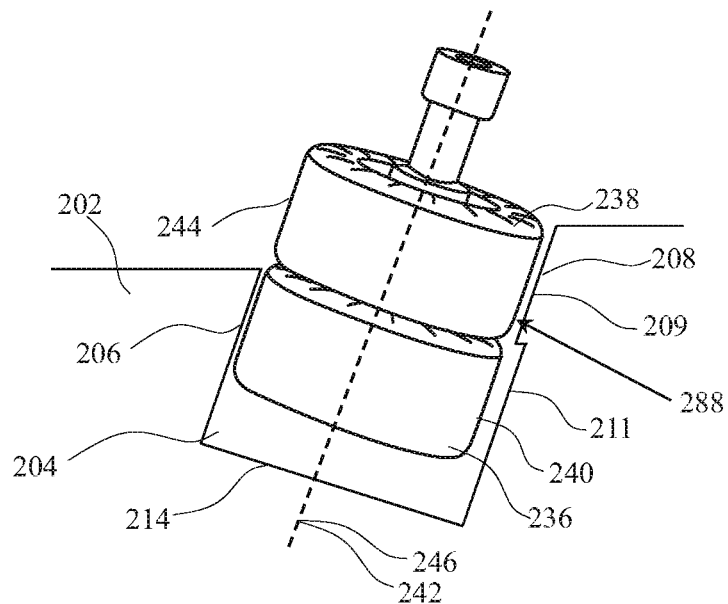
FIG. 9A is a partial front view of a slot portion and followers in accordance with one non-limiting embodiment of the present disclosure.
Figure 9B:
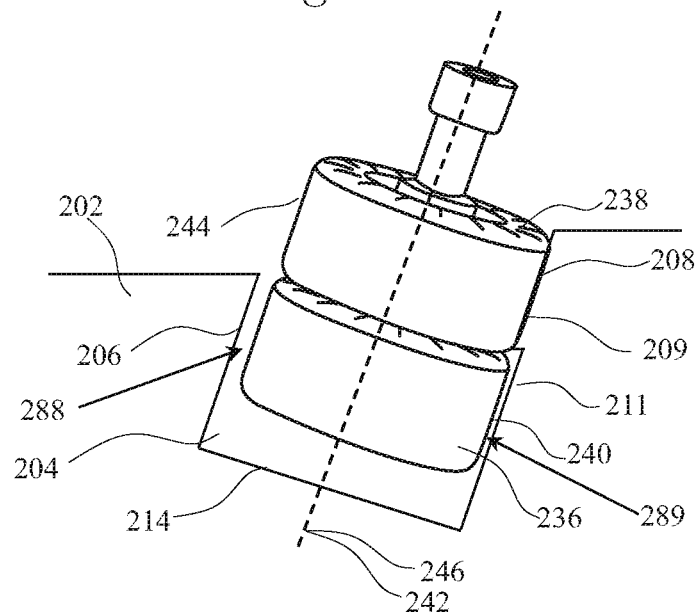
FIG. 9B is a partial front view of a slot portion and followers in accordance with one non-limiting embodiment of the present disclosure.

FIG. 8 illustrates a top view of the support member 230 including a first arm 274. The support member 230 may rotate about a rotation pathway 286. The first arm 274 may rotate a clockwise or counterclockwise direction as indicated by arrow 304 along the rotation pathway 286. As the support arm 230 rotates about the longitudinal transfer axis 224, the first follower and the second follower may engage the first slot surface and the second slot surface respectively, as illustrated in FIGS. 9A and 9B. A gap 288 may be maintained as the first follower 236 and the second follower 238 engage the first slot surface 206 and the second slot surface 208, respectively. More specifically, when the first follower 236 is engaged with the first slot surface 206, a gap 288 may be present between the second follower 238 and the second slot surface 208, as illustrated in FIG. 9A. Similarly, when the second follower 238 is engaged with the second slot surface 208, a gap 288 may be present between the first follower 236 and the first slot surface 206, as illustrated in FIG. 9B. The gap may be from about 0.01 mm to about 1 mm and/or from about 0.05 mm to about 0.90 mm and/or from about 0.3 mm to about 0.5 mm and/or from about 0.1 mm to about 0.2 mm, including all 0.01 mm increments therebetween. It is also to be appreciated that the support member 230 may be designed such that there is no gap between the followers and the first and second surfaces.

In some embodiments, the slot surface that engages the upper or, as illustrated in FIGS. 9A and 9B, second follower 238 may include an engagement surface 209 and a recessed surface 211. In some embodiments, the second slot surface 208 may include an engagement surface 209 that may associate with the second follower 238. Thus, to move the support member 230 about the longitudinal transfer axis, the engagement surface 209 of the second slot surface 208 may exert a force on the second follower 238. It is to be appreciated that the first follower 236 and the second follower 238 may rotate about their respective longitudinal follower axes in opposite directions. Thus, when the first slot surface 206 engages the first follower 236, the first follower 236 may rotate in a clockwise direction about the first longitudinal follower axis 242. Assuming that the head assembly continues to rotate in the same direction about the longitudinal slot axis 210, the second slot surface 208 may engage the second follower 238 causing the second follower 238 to rotate about the second longitudinal follower axis 246 in a counterclockwise direction. Because the first follower and the second follower are configured to rotate in opposite directions, the second slot surface 208 may include a recessed surface 211. The recessed surface 211 may be configured such that as the second follower 238 engages the second slot surface 208, a second gap 289 may be maintained between the first follower 236 and the second slot surface 208, as illustrated in FIG. 9B. The recessed surface 211 and the second gap 289 may prevent the first follower 236 from having to switch which direction the first follower 236 rotates about the first longitudinal transfer axis 242. It is to be appreciated that the first slot surface may also be designed with an engagement surface and a recessed surface.

Further, due to the angular position of the first follower 236 and the second follower 238, as illustrated in FIGS. 7, 9A, and 9B the first slot surface 206 and the second slot surface 208 may be such that the first slot surface 206 is parallel to the first follower outer surface 240 and the second slot surface 208 is parallel to the second follower outer surface 244. For example, as shown in FIGS. 9A and 9B, the angle of the first slot surface 206 and the angle of the second slot surface 208 with respect to the longitudinal slot axis 210 may change as the position of the support member 230 changes about the rotation pathway 286.

Figure 11:
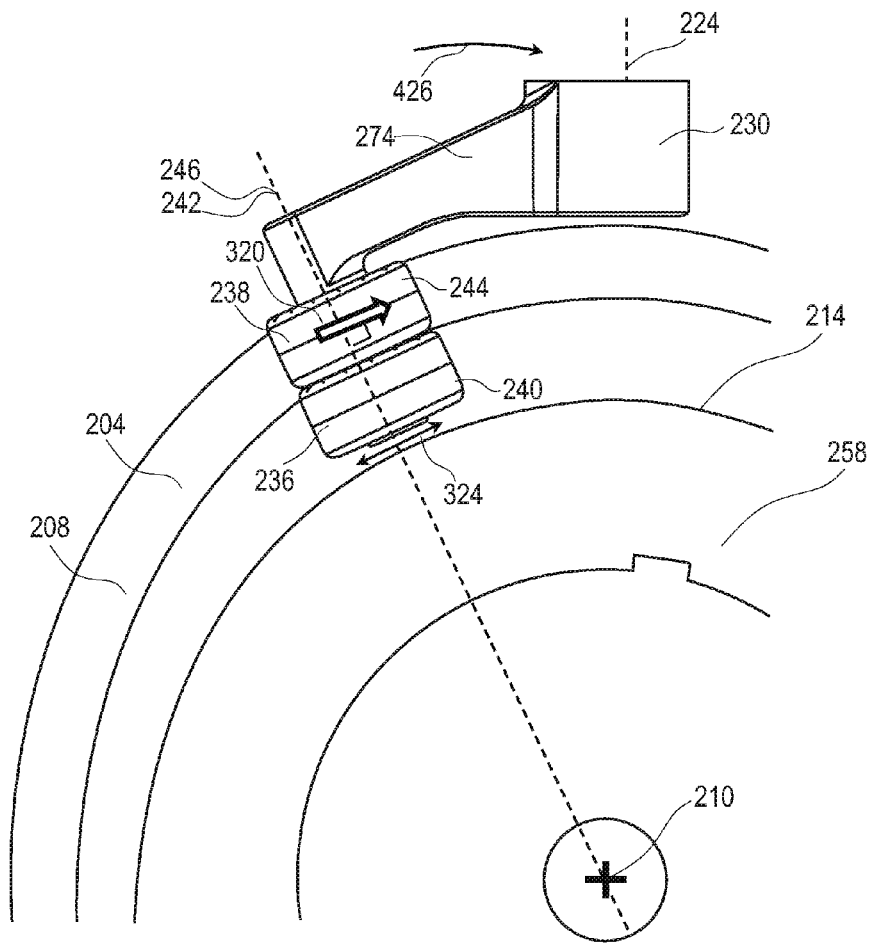
FIG. 11 is a schematic, partial representation of a rotation apparatus in accordance with one non-limiting embodiment of the present disclosure.

As previously discussed with reference to FIG. 7, the support member 230 may be positioned at a vertical arm angle α with respect to the longitudinal transfer axis 224. Thus, the first follower 236 and the second follower 238 may be positioned at a follower angle δ. It is to be appreciated that the longitudinal transfer axis 224 may not intersect the longitudinal slot axis 210. However, the angle δ may be measured from an axis extending perpendicular to the longitudinal slot axis 210 to each of the first longitudinal follower axis 242 and the second longitudinal follower axis 244. The first follower 236 and the second follower 238 may be positioned such that the first longitudinal follower axis 242 and the second longitudinal follower axis 246 intersect the longitudinal slot axis 210. The position of the first follower 236 and the second follower 238 also may result in a reduction in forces exerted on the followers 236, 238. To appreciate how the rotation apparatus 200 may relatively reduce the force on the followers, FIG. 10A illustrates a device previously used and FIG. 11 illustrates a rotation apparatus 200 as disclosed herein.

FIG. 10A illustrates a device 450 that has been previously used to, for example, transfer products such as disclosed in U.S. Pat. No. 6,758,109. The device 450 may include an arm 400 and an upper follower 402 and a lower follower 403 connected thereto. The upper and lower followers 402, 403 may rotate about a longitudinal follower axis 418, which is not positioned to intersect the rotational axis 424. The arm 400 may be positioned such that at least one of the upper follower 402, as shown in FIG. 10A, and the lower follower 403 engages the cam device 420. The cam device 420 may include a sidewall 422 that is configured to exert a force on the upper follower 402 to control the position of the follower 402 and the arm 400.

The cam device 420 may define a rotational axis 424 about which that arm 400, including the upper and lower followers 402, 403, may rotate. Thus, the arm 400 and the followers 402, 403 may rotate in a direction indicated by arrow 426. Due to the position of the followers 402, 403 and the rotational direction 426 of the arm and the followers 402, 403, the sidewall 422 may exert a resultant radial force 428 on the follower 402. The resultant radial force 428 is generally in the direction of rotation of the arm 400 and the followers 402, 403. However, the followers 402, 403 are restricted from rotating in a direction parallel to the resultant radial force 428. The followers 402, 403 rotate in a follower rotational direction, indicated by arrow 430, which may be perpendicular to the longitudinal follower axis 418. Thus, the upper follower 402 and/or the lower follower 403 may slide against the sidewall 422.

The resultant radial force 428 may act in a direction perpendicular to a rotational radial axis 442. The rotational radial axis 442 may be a longitudinal axis that intersects the rotational axis 424 and the mid-point follower axis 444. The mid-point follower axis 444 may be positioned between the top outer follower surface 446 and the bottom outer follower surface 448.

As shown in FIG. 10B, the resultant radial force 428 may be resolved into an x-component radial force 432 and a y-component axial force 434. The x-component radial force 432 generally results in the rotation of the follower 402 about the longitudinal follower axis 418. The y-component axial force 434 generally results in wear on the follower 402 because the follower 402 is not configured to move in this direction. The y-component axial force 434 may cause the follower 402 to fail more quickly during use. Further, having to design the follower 402 to withstand this additional force may limit the number and/or type of materials that may be used to make the followers. Further still, manufacturers have used lubricants to counteract the wear on the follower due to the y-component axial force. The use of lubricants adds additional cost to the manufacturing process and may lead to contamination of the products being manufactured.

It is to be appreciated that a resultant radial force may also be exerted on the lower follower 203 by a sidewall of the cam device. This resultant radial force may also include an x-component radial force and a y-component axial force, which may not be equal in magnitude to the x-component radial force and the y-component axial force exerted on the upper follower. Thus, the lower follower must also be made to withstand these additional forces and, thus, the type and/or number of materials that may be used is limited.

The disclosed rotational device 200 solves the aforementioned problems. FIG. 11 illustrates a portion of a rotation apparatus 200, as previously discussed. The support member 230 and the follower 236 may rotate about the longitudinal slot axis 210 of rotation. Arrow 426 indicates the direction of rotation of the support member 230 and the follower 236 about the longitudinal slot axis 210. The slot portion 204 engages the followers 236, 238. More specifically, as illustrated in FIG. 11, the second slot surface 208 may exert a resultant force 320 on the second follower 238. The second follower 238 may be configured to rotate about the second longitudinal follower axis 246, as indicated by the follower rotational direction arrow 324. The follower rotational direction 324 may be generally perpendicular to the second longitudinal follower axis 246 of rotation, which intersects the longitudinal slot axis 210. Due to the position of the longitudinal follower axis 246, the resultant radial force 320 may be parallel to the follower rotational direction 324.

More specifically, due to the second longitudinal follower axis 246 being positioned to intersect the longitudinal slot axis 210, the follower rotational direction 324 may be parallel to the resultant radial force 320 exerted on the follower 238 by the second slot portion 208. Because the follower rotational direction 324 is parallel to the axial force 320, the follower may experience an x-component radial force and minimal to no y-component axial force. The reduction or elimination of y-component axial force reduces the wear on the follower because the slot portion is not exerting a force on the follower in a direction other than the follower rotational direction 324. This may allow the follower to be used for longer periods of time and may allow manufacturers to use a broader array of materials to make the follower. Further, manufacturers may eliminate or reduce the use of lubricants because there is no y-component axial force to counteract.

It is to be appreciated that the reduction in y-component axial force may be the same for the first follower 236, which engages the first slot surface 206 in a similar manner.

Figure 12:
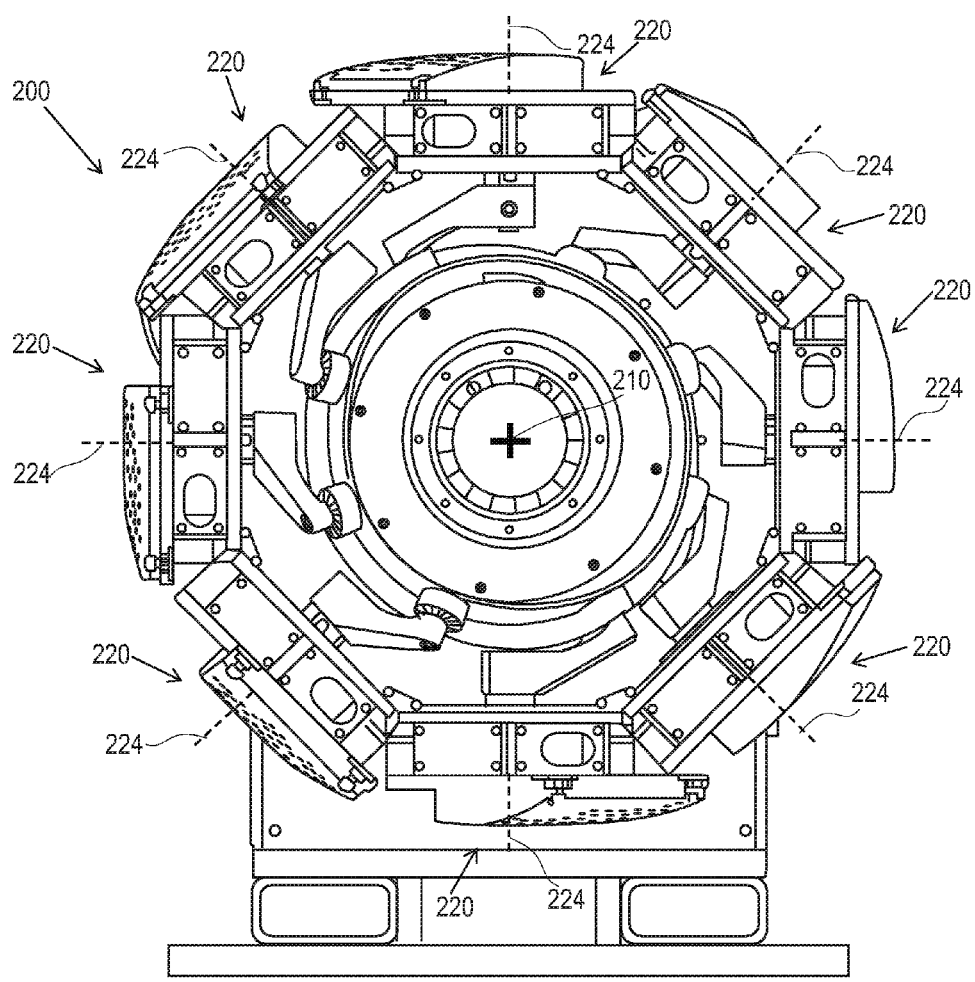
FIG. 12 is a side view of a rotation apparatus in accordance with one non-limiting embodiment of the present disclosure.

Referring to FIG. 12, the rotation apparatus 200 may include one or more head assemblies 220 configured to rotate about the longitudinal slot axis 210 of rotation. Each head assembly 220 may be configured as previously disclosed. Further, a portion of each head assembly 220, as previously disclosed, may be configured to rotate about the longitudinal transfer axis 224. The number and size of the articles to be transferred and rotated may determine the size of each of the rip portion 204 and the head assembly 220. In some embodiments, each head assembly 220 may be rotated using, for example, an electric servo motor, or hydraulic or pneumatic actuators.

Figure 13B:
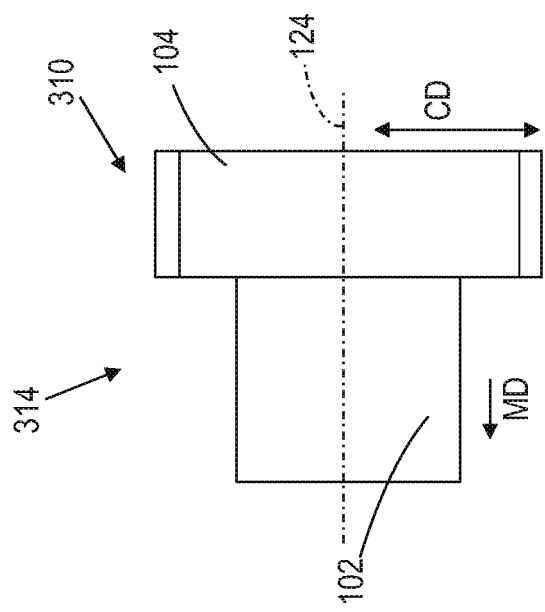
FIG. 13B is a schematic, plan view of a folded diaper in a second orientation in accordance with one non-limiting embodiment of the present disclosure.

The rotation apparatus 220 operates to change the orientation of a folded diaper 310 as the folded diaper 310 advances in the machine direction MD. With reference to FIGS. 14A and 14B, the rotation apparatus 200 operates to change the orientation of the folded diaper 310 from a first orientation 312 to a second orientation 314. As shown in FIG. 14A, in the first orientation 312, the longitudinal centerline 124 of folded diaper 310 may extend in the cross direction CD. The folded diaper 310 may rotate about the longitudinal transfer axis 224 to a second orientation 314. As shown in FIG. 13B, in the second orientation 314, the longitudinal centerline 124 of the folded diaper 310 may extend in the machine direction MD.

Figure 14:
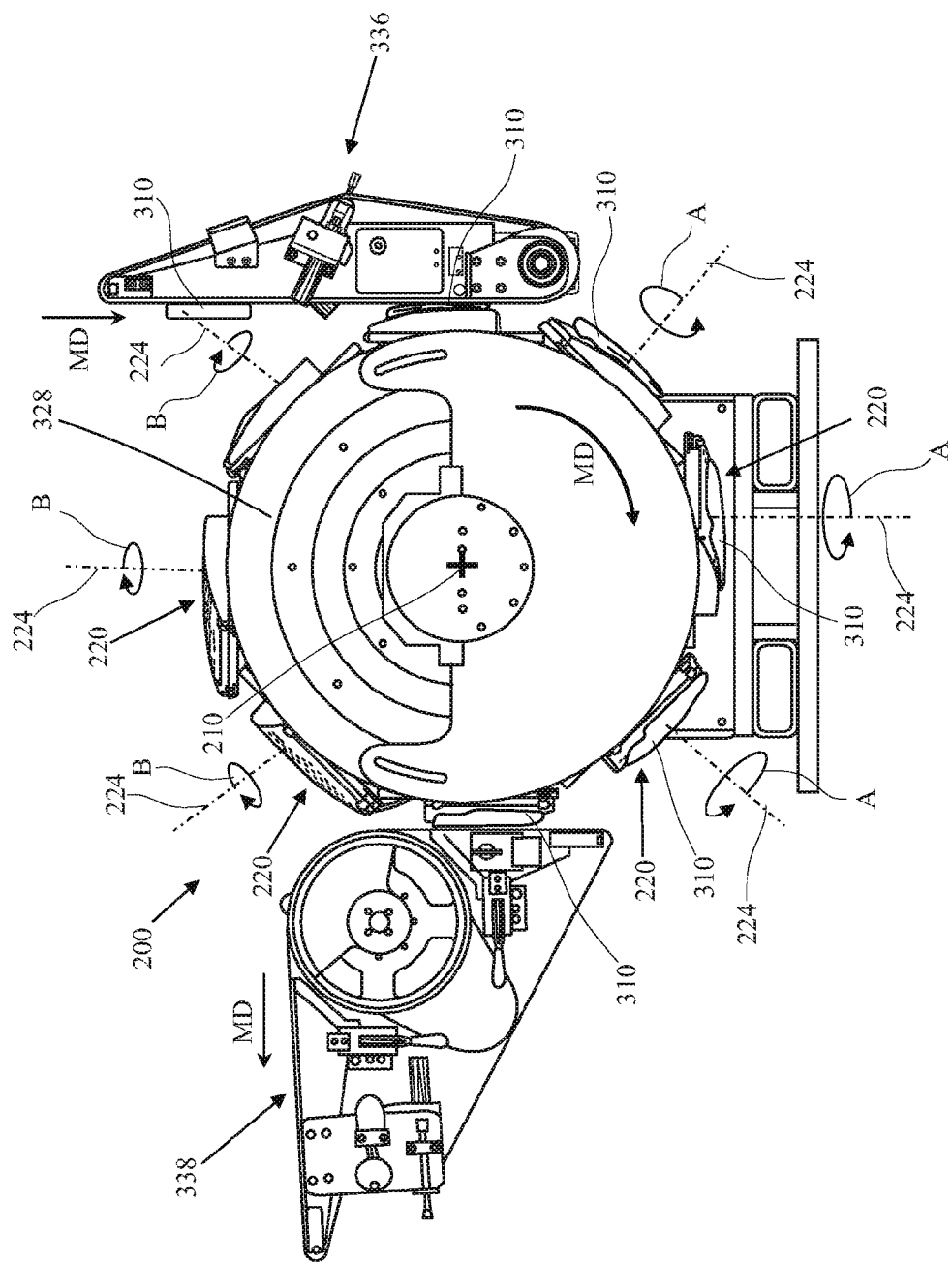
FIG. 14 is a side view of a rotation apparatus in accordance with one non-limiting embodiment of the present disclosure.

As shown in FIG. 14, the rotation apparatus 200 may include a frame 328 and a plurality of head assemblies 220 connected with the frame 328. More specifically, the connection member 248, as illustrated in FIG. 4, of the head assembly 220 may associated with the frame 328. The frame 328 may be adapted to rotate about a longitudinal slot axis 210 of rotation that extends in a first direction. A portion of the head assemblies 220 are adapted to rotate about a longitudinal transfer axis 224 of rotation that extends in a second direction that is different from the first direction. For example, the longitudinal slot axis 210 may be orthogonal to the longitudinal transfer axis 224. Each head assembly 220 may be configured to advance a folded diaper 310 from the first carrier apparatus 336 to the second carrier apparatus 338.

Figure 15B:
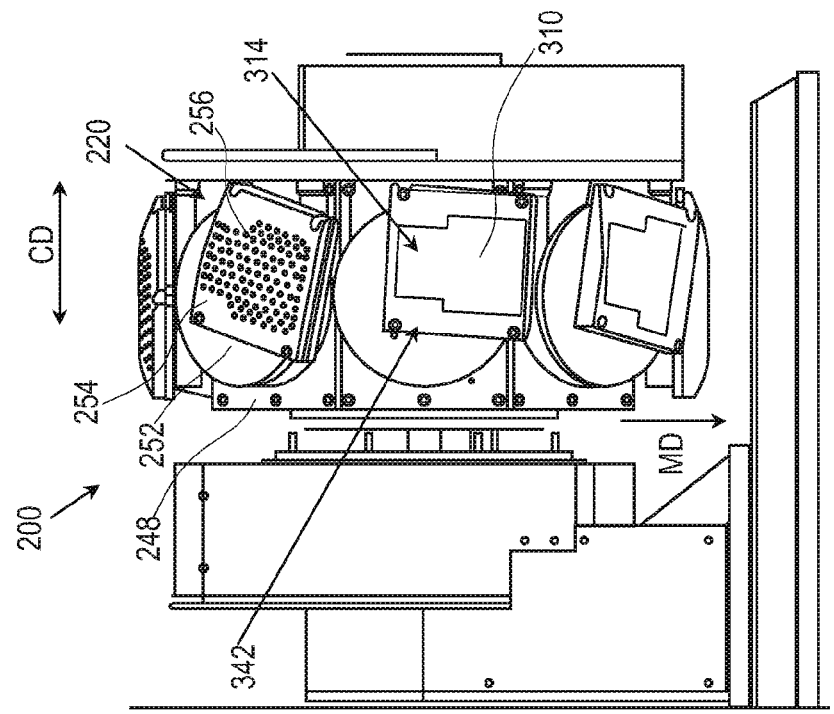
FIG. 15B is a side view of a rotation apparatus in accordance with one non-limiting embodiment of the present disclosure.
Figure 15A:
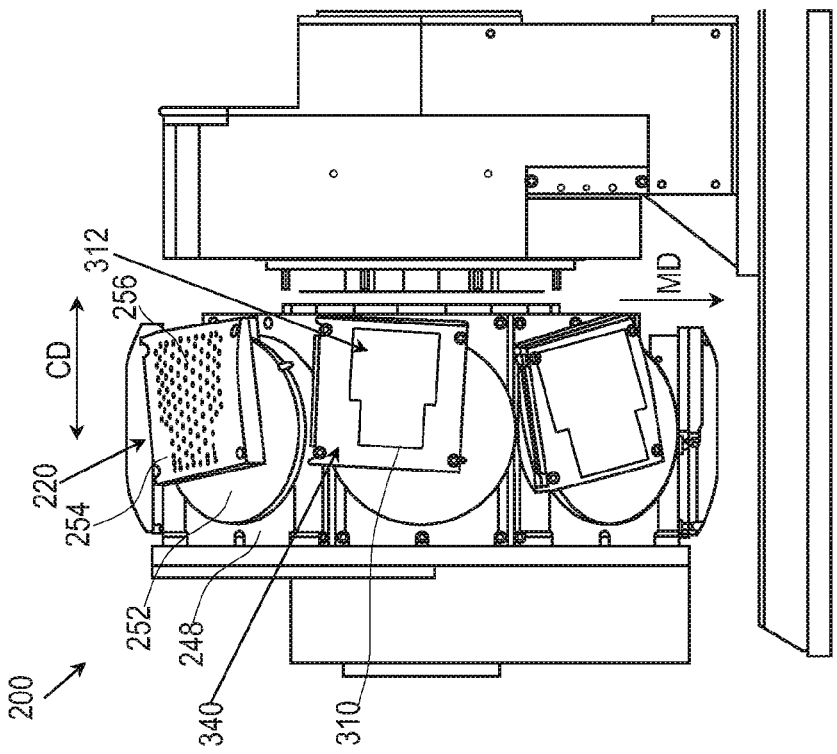
FIG. 15A is a side view of a rotation apparatus in accordance with one non-limiting embodiment of the present disclosure.

In operation, the frame 328 rotates about the longitudinal slot axis 210 of rotation and a portion of the head assembly 220 rotates about the longitudinal transfer axis 224 of rotation. A folded diaper 310 may advance on to a first carrier apparatus 336 adjacent to the rotation apparatus 200. The folded diaper 310 may be transferred from the first carrier apparatus 336 and onto the receiving member 254 of the head assembly 220 as the head assembly 220 rotates adjacent to the first carrier apparatus 336. When the folded diaper 310 advances onto the receiving member 254 of the head assembly 220, the folded diaper 310 may be oriented in the first orientation 312 and, thus, the transfer member 230 may be in a first position 340, such as shown in FIG. 15A. The frame 328 continues rotating about the longitudinal slot axis 210 of rotation and a portion of the head assembly 220 rotates the folded diaper 310 about the longitudinal transfer axis 224 of rotation. The folded diaper 310 may advance on the head assembly 220 until the head assembly 220 is positioned in a second position 342 and the folded diaper 310 is at the second orientation 314, such as shown in FIG. 15B. The folded diaper 310 may then be transferred from the head assembly 220 onto the second carrier apparatus 338, which may be located adjacent to the rotation apparatus 200 as shown in FIG. 14.

Figure 13A:
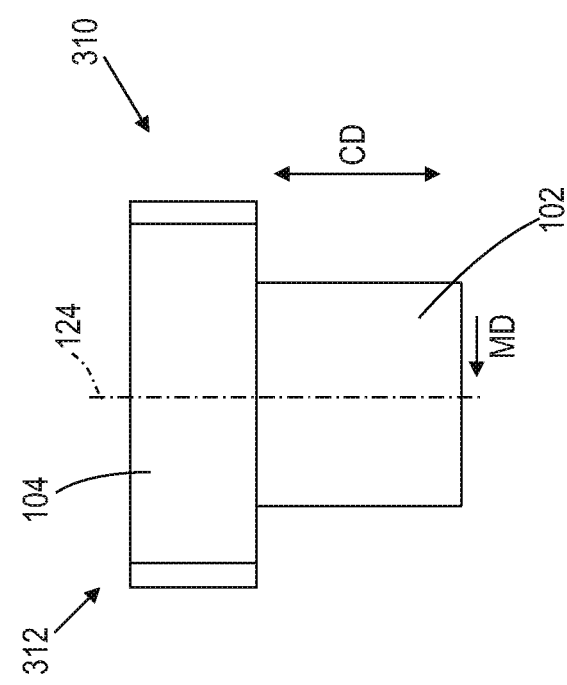
FIG. 13A is a schematic, plan view of a folded diaper in a first orientation in accordance with one non-limiting embodiment of the present disclosure.

As illustrated in FIGS. 13A and 13B, the receiving member 254 may be configured to hold the discrete article thereto using fluid pressure, magnets, or an adhesive, for example. In some exemplary configurations, the receiving member 254 may include a plurality of apertures 256 defined in the receiving member 254. The apertures 256 may be in gaseous communication with a vacuum source for retaining the discrete articles on the receiving member 254 as the frame 328 and/or the head assembly 220 rotate about the longitudinal slot axis 210 and the longitudinal transfer axis 224. As shown in FIGS. 13A and 13B, the apertures 256 may be arranged in the shape of a folded diaper 310. However, it is to be appreciated that the apertures 256 may be arranged in various other configurations. The apertures 256 may also be used to apply a positive pressure to the discrete articles on the receiving member 254. The positive pressure may be used, for example, to assist in the removal of the folded diaper 310 from the receiving member 254.

In some exemplary configurations, a portion of the head assembly 220 may rotate from a first position 340 to a second position 342 while advancing the folded diaper 310 from the first carrier apparatus 336 to the second carrier apparatus 338. As a result, the folded diaper 310 may rotate from the first orientation 312 to the second orientation 314. In some exemplary configurations, a portion of the head assembly 220 may continuously rotate from about 80° to about 100° from the first position 340 to the second position 342. In some exemplary configurations, a portion of the head assembly 220 may rotate 360° from the first position 340, through the second position 342, and back to the first position 340. In some exemplary configurations, a portion of the head assembly 220 may rotate 90° in a first direction A about the longitudinal transfer axis 224 and may be configured to subsequently rotate 90° in a second direction B about the longitudinal transfer axis 224, as illustrated in FIG. 14. Thus, the folded diaper 310 may be rotated at various rotation angles from the first orientation 312 shown in FIG. 13A to the second orientation 314 shown in FIG. 13B. For example, the folded diaper 310 may be rotated about 90° (for example, +/−5°), or between about 80° and 100° from the first orientation 312 to the second orientation 314. The head assembly 220 may be configured to rotate the receiving member 254 in various ways. For example, the frame 328 may be rotated using an electric servo motor, hydraulic or pneumatic actuators, or mechanical cams, for example, which in turn may rotate each head assembly 220, which may be associated with the frame 328.

The frame 328 of the rotation apparatus 200 may be configured to continuously rotate about the longitudinal slot axis 210 of rotation. The frame 328 may rotate at a constant angular velocity such that the speed at the receiving member 254 is constant. In some exemplary configurations, the frame 328 may rotate at a variable angular velocity such that the speed at the receiving member 254 is variable. In some exemplary configurations, the frame 328 may rotate about 180° to transfer a folded diaper from a first carrier apparatus 336 to the second carrier apparatus 338. The frame 328 may rotate at various rotation angles to transfer the folded diaper from a first carrier apparatus 336 to the second carrier apparatus 338. In such an exemplary configuration, the frame 328 may rotate a head assembly 220 about 180° about the longitudinal slot axis 210 in the same direction to pick up a subsequent folded diaper from the first carrier apparatus 336.

The first and second carrier apparatuses 336, 338 from and to which the folded diaper 310 are transferred may be rolls, drums, curved conveyors, linear conveyors, and/or discrete heads following a curvilinear path, for example. The first and second carrier apparatuses 336, 338 may be moving at a different surface velocity or at the same surface velocity. The first and second carrier members 336, 338 may be configured to apply negative, vacuum pressure and/or positive, blow-off pressure to the folded diaper 310. In some exemplary configurations, the head assembly may rotate the folded diaper and then subsequently shift the cross-directional position of the folded diaper. For example, the head assembly may be driven by two separate actuators; one actuator may rotate a portion of the head assembly, and the second actuator may shift a portion of the head assembly such that the cross-directional position of the folded diaper shifts.

In some exemplary configurations, one head assembly 220 may rotate in a first direction A and a subsequent head assembly 220 may rotate in a second direction B. As such, it is to be appreciated that a rotation apparatus 200 may be used to rotate one folded diaper in the first direction A and to rotate the next folded diaper in the second direction B.

Figure 16:
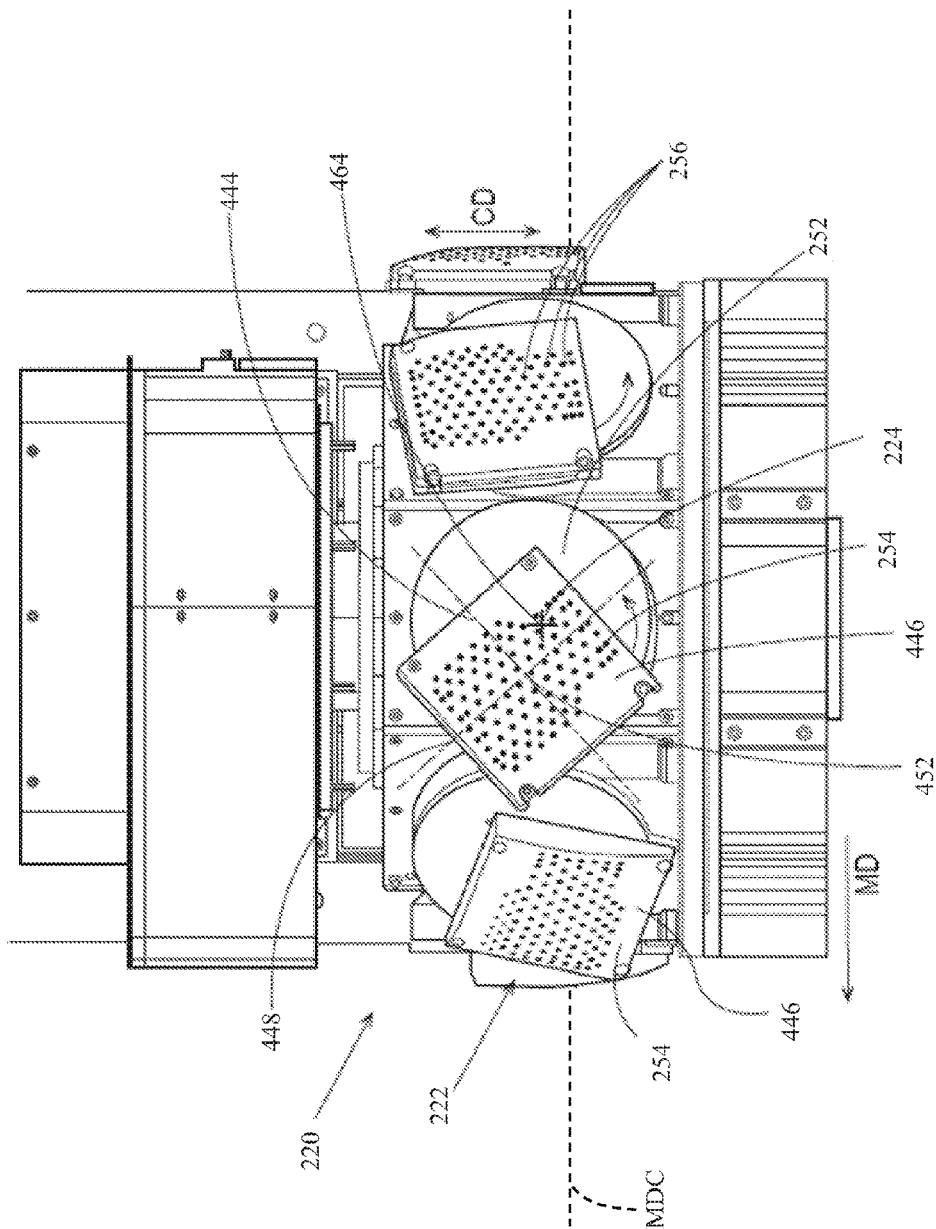
FIG. 16 is a top view of a rotation apparatus in accordance with one non-limiting embodiment of the present disclosure.

Referring to FIG. 16, each head assembly 220 may include a receiving member 254 having a receiving surface 446 located on an end of the head assembly 220 most distal from the longitudinal slot axis 210. The receiving surface 446 may be defined by a first centerline 448 and a second centerline 444 that intersect at a center 452 of the receiving surface 446. In some exemplary configurations, the center 452 of the receiving surface 446 may be offset from the longitudinal transfer axis 224, such as shown in FIG. 16. The receiving surface 446 may be curved, or partially curved in one or more directions. However, in some exemplary configurations, the receiving surface may be flat, or substantially flat in one or more directions. As shown in FIG. 16, the receiving surface 446 may be substantially rectangular in shape; however, it is to be appreciated that the receiving surface may form various other shapes, such as squares, circles, or ovals for example. The receiving surface 446 may be configured to receive one or more folded diaper 310.

The head assembly 220 may also include a rotation member 252 as shown in FIG. 16. The rotation member 252 may be defined by a center 464. The rotation member 262 may be operatively connected with the receiving member 254. The receiving member 254 and the rotation member 252 may be separate elements, or in some exemplary configurations, the receiving member 254 and the rotation member 252 may be a single, continuous element. The longitudinal transfer axis of rotation 224 may align with the center 464 of the rotation member 252, such as shown in FIG. 16. In such an exemplary configuration, the folded diaper may be positioned on the receiving surface 446 of the receiving member 254 such that the center of the folded diaper is substantially aligned with the center 452 of the receiving member 254. It is to be appreciated that in some exemplary configurations the center 464 of the rotation member 252 may be offset from the longitudinal transfer axis of rotation 224. While it is shown in FIG. 16 that the rotation member 252 is substantially circular, it is to appreciated that the rotation member may have various shapes and configurations.

The rotation apparatus 200 may include eight head assemblies 220 as shown in FIG. 12. However, it is to be appreciated that the rotation apparatus 200 may include various numbers of head assemblies 220 that are each configured to rotate and shift a folded diaper from a first orientation to a second orientation.

Figures 17A, 17B:
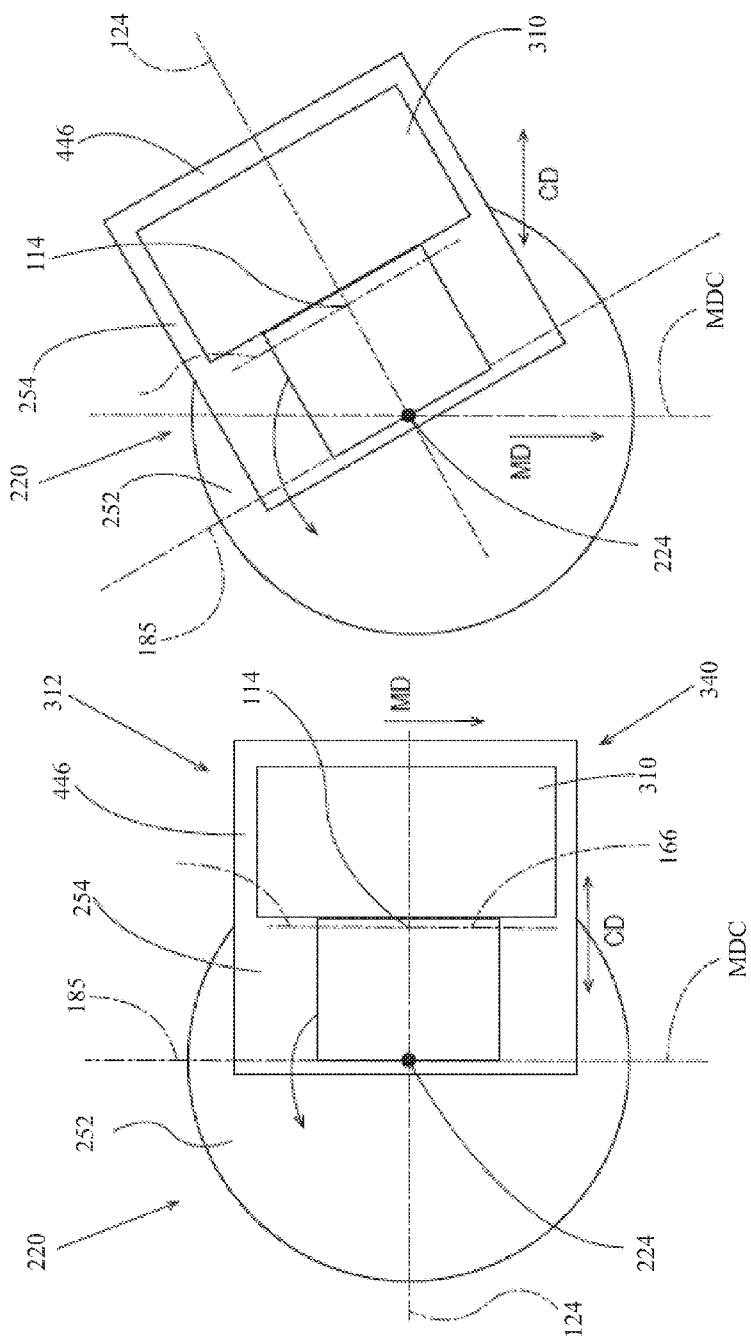
FIG. 17A is a schematic, plan view of a portion of the head assembly in accordance with one non-limiting embodiment of the present disclosure.
FIG. 17B is a schematic, plan view of a portion of the head assembly in accordance with one non-limiting embodiment of the present disclosure.
Figures 17C, 17D:
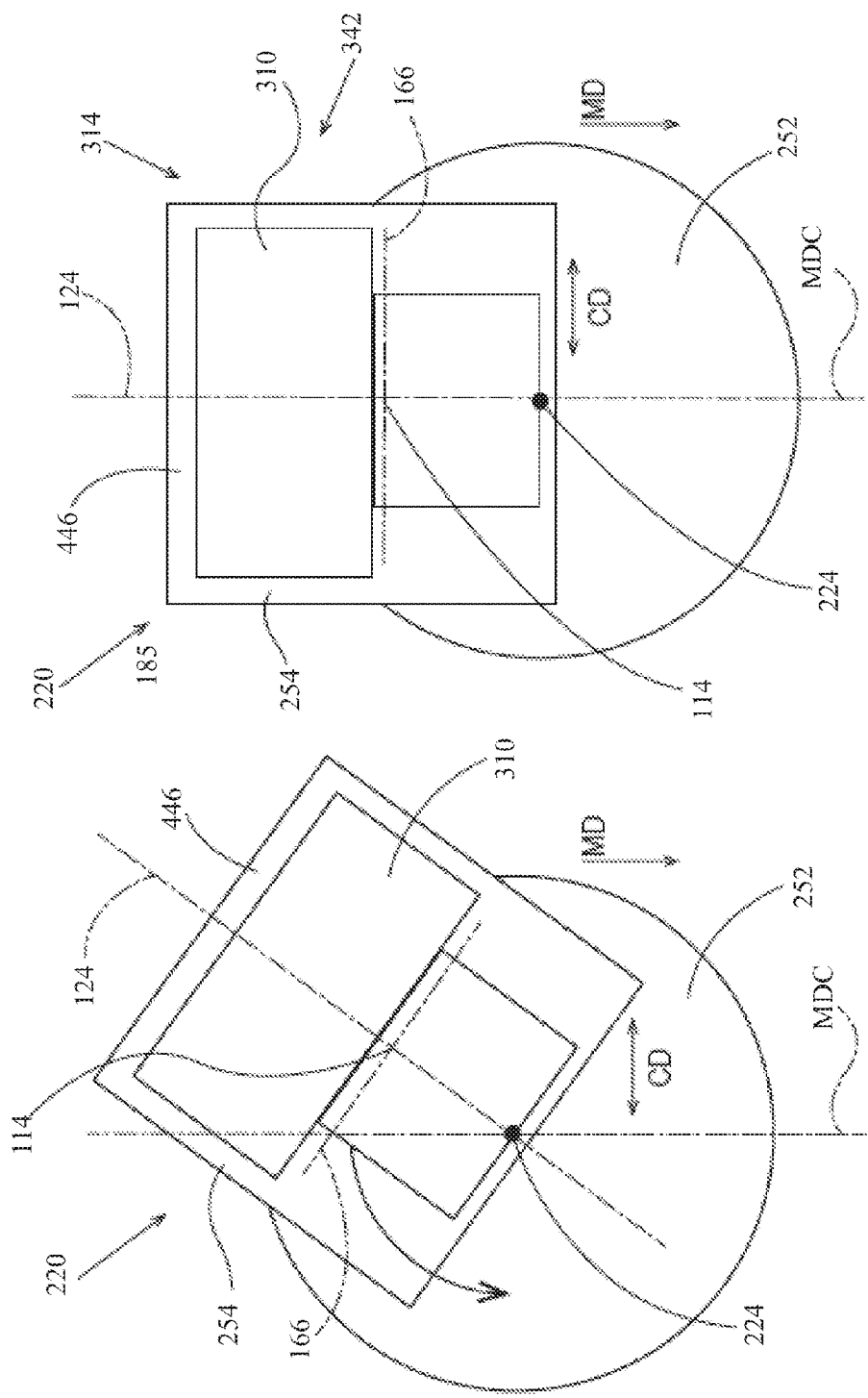
FIG. 17C is a schematic, plan view of a portion of the head assembly in accordance with one non-limiting embodiment of the present disclosure.
FIG. 17D is a schematic, plan view of a portion of the head assembly in accordance with one non-limiting embodiment of the present disclosure.

As shown in FIG. 17A, in a first orientation 312, the folded diaper 310 may be arranged such that the lateral fold line 185 is aligned with and extends along the machine direction centerline MDC and the center 114 of the folded diaper 310 is located in a first cross-directional position away from the machine direction centerline MDC. The head assembly 220 shown in FIG. 17A is in a first position 340. As shown in FIGS. 17B and 17C, the rotation member 252 rotates about the longitudinal transfer axis of rotation 224 and the center 114 of the folded diaper 310 shifts in the cross direction CD. As shown in FIG. 17D, the folded diaper 310 is located in a second orientation 314 and the rotation member 252 is located in a second position 342. As a result of rotating the folded diaper 310 about the longitudinal transfer axis of rotation 224, the folded diaper 310 may shift from the first orientation 312 to the second orientation 314 where the center 114 of the folded diaper 310 is aligned with the machine direction centerline MDC. In the second orientation 314 shown in FIG. 17D, the folded diaper 310 is also rotated such that the longitudinal centerline 124 extends in the machine direction MD.

In some exemplary configurations, the head assembly may rotate the folded diaper and then subsequently shift the cross-directional position of the center of the folded diaper. For example, the head assembly may be driven by two separate actuators; one actuator may rotate the rotation member of the head assembly, and the second actuator may shift the receiving member such that the cross-directional position of the center of the folded diaper shifts.

The folded diaper 310 may be positioned in various configurations with respect to the longitudinal transfer axis of rotation. For example, as shown in FIGS. 17A-17D, the longitudinal transfer axis of rotation 224 may align with the intersection of the longitudinal centerline 124 and the lateral fold line 185 of the folded diaper 310. In such exemplary configurations, the longitudinal centerline 124 of the folded diaper 310 may align with the machine direction centerline MDC when the folded diaper 310 is rotated to the second orientation 314. It is to be appreciated that the folded diaper 310 may be arranged in various configurations at the second orientation 314 depending upon the desired orientation of the folded diaper 310 when the folded diaper 310 is transferred to the second carrier apparatus.

Figures 18A, 18B:
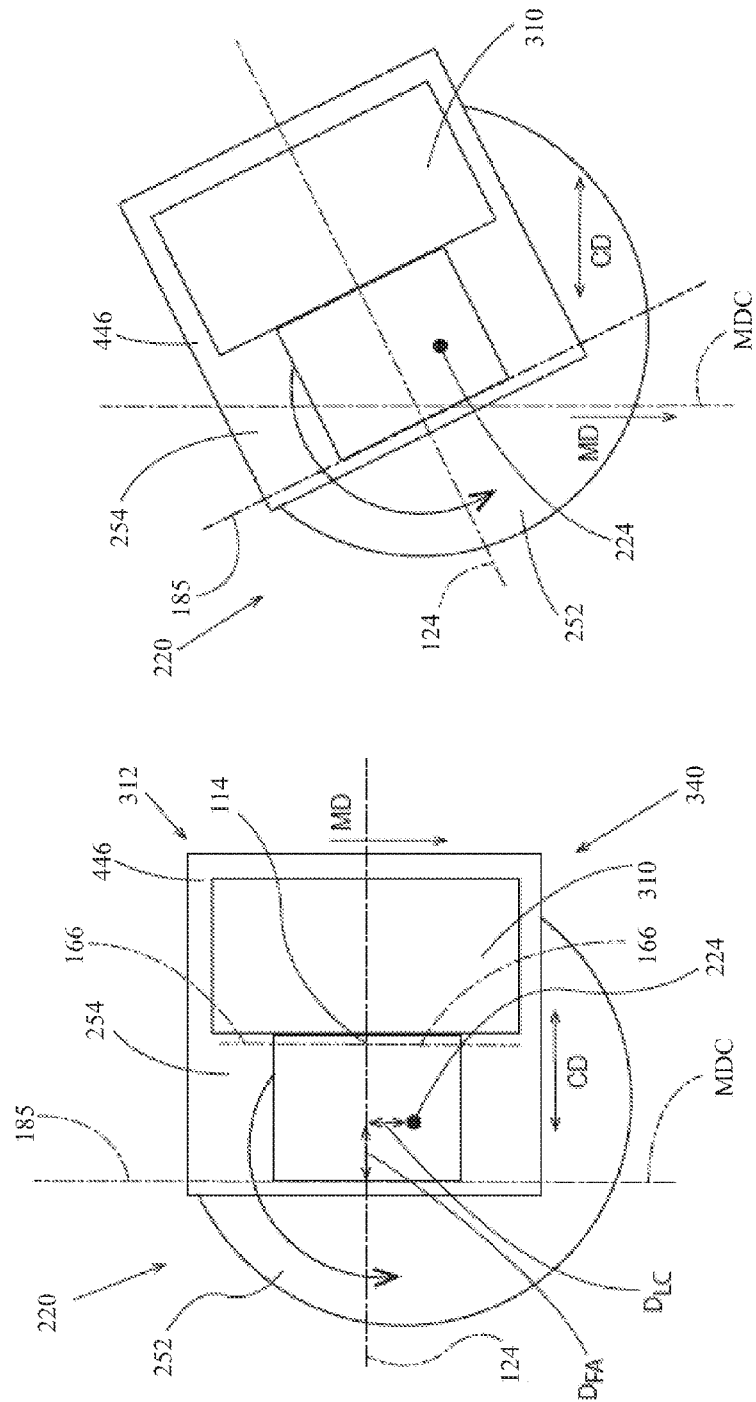
FIG. 18A is a schematic, plan view of a portion of the head assembly in accordance with one non-limiting embodiment of the present disclosure.
FIG. 18B is a schematic, plan view of a portion of the head assembly in accordance with one non-limiting embodiment of the present disclosure.
Figures 18C, 18D:
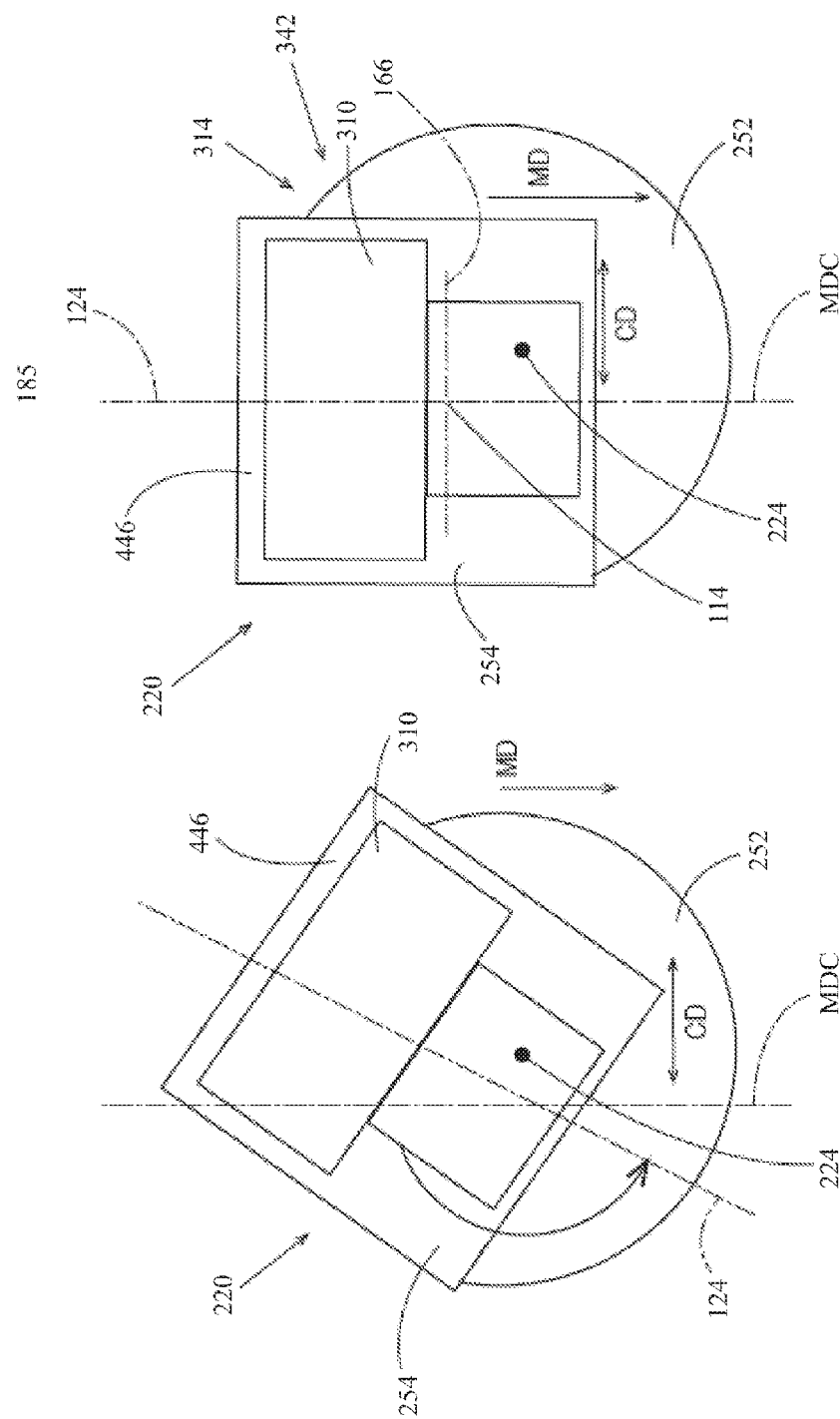
FIG. 18C is a schematic, plan view of a portion of the head assembly in accordance with one non-limiting embodiment of the present disclosure.
FIG. 18D is a schematic, plan view of a portion of the head assembly in accordance with one non-limiting embodiment of the present disclosure.

FIGS. 18A-18D show another exemplary configuration for a head assembly 220. As shown in FIG. 18A, the longitudinal transfer axis of rotation 224 may be located a first distance $D_{FA}$ from the lateral fold line 185 and a second distance $D_{LC}$ from the longitudinal centerline 124, where the first distance $D_{FA}$ and the second distance $D_{LC}$ are equal. As shown in FIG. 18D, in such an exemplary configuration, the longitudinal centerline 124 of the folded diaper 310 may align with the machine direction centerline MDC when the folded diaper 310 is rotated to the second orientation 314. It is to be appreciated that in a configuration where the lateral fold line 185 is aligned with the machine direction centerline MDC at the first orientation 312, the longitudinal transfer axis of rotation 224 may be aligned with various points on the folded diaper 310 where the first distance $D_{FA}$ and the second distance $D_{LC}$ are equal. In such configurations, the longitudinal centerline 124 may be positioned along the machine direction centerline MDC when the folded diaper 310 is rotated to the second orientation 314.

It is to be appreciated that in some exemplary configurations, the center 452 of the receiving surface 446 may align with the longitudinal transfer axis of rotation 224. In such an exemplary configuration, the folded diaper 310 may cover only a portion of the receiving surface 446. The folded diaper 310 may be positioned on the receiving surface 446 such that the lateral fold line 185 and the longitudinal centerline 124 of the folded diaper 310 intersect at the longitudinal transfer axis of rotation 224.

While the methods and apparatuses disclosed herein operate to transfer and rotate a folded diaper, it is to be appreciated that the methods and apparatuses disclosed herein may also be used in various other processes in the manufacture of absorbent articles. In one exemplary configuration, the methods and apparatuses disclosed herein may be used to transfer and rotate discrete diaper chassis. More specifically, the methods and apparatuses disclosed herein may be used with the methods and apparatuses for transferring and rotating a discrete chassis disclosed in U.S. Patent Publication Nos. 2013/0270065; 2013/0270066; 2014/0112751; 2014/0113793; and U.S. Pat. Nos. 8,607,959; 8,720,666.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rotation apparatus for rotating a discrete article, the rotation apparatus comprising:
   a slot portion defined by a mounting surface, the slot portion comprises a first slot surface, a second slot surface opposite the first slot surface, and an inner slot surface extending between the first slot surface and the second slot surface, wherein the slot portion defines a longitudinal slot axis of rotation;
   a head assembly positioned adjacent to the slot portion, wherein the head assembly comprises a transfer member having a proximal end portion and a distal end portion, wherein the transfer member defines a longitudinal transfer axis of rotation, and wherein at least a portion of the head assembly is configured to rotate about the longitudinal transfer axis;
   a support member extending from the transfer member toward the slot portion, the support member having a proximal end portion and a distal end portion opposite the proximal end portion, wherein the proximal end portion of the support member is associated with the distal end portion of the transfer member;

a first follower and a second follower operatively engaged with the distal end portion of the support member, wherein the first follower comprises a first follower outer surface and the second follower comprises a second follower outer surface, and wherein the first follower outer surface and the second follower outer surface define a longitudinal follower axis, wherein the longitudinal follower axis intersects the longitudinal slot axis, and wherein the longitudinal follower axis forms an angle between about 5 and about 60 degrees with the longitudinal transfer axis.

2. The rotation apparatus of claim 1, wherein the slot portion comprises a slot width, wherein the slot width is non-uniform as the slot portion extends around the mounting surface.

3. The rotation apparatus of claim 1, wherein the mounting surface comprises a first face, a second face opposite the first face, and an outer mounting surface extending between the first face and the second face, wherein the slot portion extends around the outer mounting surface and separates the outer mounting surface into a first mounting portion and a second mounting portion, wherein the first mounting portion has a first radius extending from the longitudinal slot axis to the first mounting portion and the second mounting portion has a second radius extending from the longitudinal slot axis to the second mounting portion.

4. The rotation apparatus of claim 3, wherein the first radius is less than the second radius.

5. The rotation apparatus of claim 1, wherein the first follower engages the first slot surface.

6. The rotation apparatus of claim 1, wherein the second slot surface comprises an engagement surface and a recessed surface, wherein the engagement surface is positioned to associate with the second follower and the recessed surface is positioned to define a second gap between the recessed surface and the first follower.

7. The rotation apparatus of claim 1, wherein the longitudinal transfer axis intersects the longitudinal slot axis.

8. The rotation apparatus of claim 1, wherein the support member comprises a first arm, and wherein the first arm forms a vertical arm angle with the longitudinal transfer axis.

9. The rotation apparatus of claim 1, wherein the first follower and the second follower are adapted to rotate about the longitudinal follower axis.

10. The rotation apparatus of claim 1, wherein the slot portion includes at least one of a motion zone and a dwell zone.

11. The rotation apparatus of claim 1, wherein at least one of the first follower and the second follower are made of a polymer.

12. The rotation apparatus of claim 1, wherein at least one of the first follower and the second follower are made of a non-metallic material.

13. The rotation apparatus of claim 1, further comprising a frame configured to rotate about the longitudinal slot axis.

14. The rotation apparatus of claim 13, wherein the head assembly comprises a connection member associated with the proximal end portion of the transfer member and associated with a portion of the frame.

15. The rotation apparatus of claim 1, wherein the head assembly comprises a brace member associated with the proximal end portion of the transfer member.

16. The rotation apparatus of claim 1, wherein the head assembly comprises a rotation member associated with the proximal end portion of the transfer member, wherein the transfer member and the rotation member are adapted to rotate about the longitudinal transfer axis.

17. The rotation apparatus of claim 16, wherein the head assembly comprises a receiving member associated with the rotation member, wherein the receiving member is adapted to receive a discrete article.

18. The rotation apparatus of claim 1, further comprising a gap between at least one of the first outer follower surface and the first slot surface and the second outer follower and the second slot surface.

19. A method of transferring and rotating discrete substrates, the method comprising:

advancing a discrete substrate in a machine direction;

providing a rotation apparatus comprising slot portion defined by a mounting surface, the slot portion comprising a first slot surface, a second slot surface opposite the first slot surface, and an inner slot surface extending between the first slot surface and the second slot surface, wherein the slot portion defines a longitudinal slot axis of rotation;

rotating a head assembly about the longitudinal slot axis, wherein the head assembly is adjacent the slot portion, and wherein the head assembly comprises a transfer member defining a longitudinal transfer axis of rotation and a support member associated with a distal end portion of the transfer member;

rotating the transfer member about a longitudinal transfer axis;

rotating a support member about the longitudinal transfer axis, wherein the support member extends from the transfer member toward the slot portion;

associating a first follower and a second follower with the slot portion, wherein the first follower and the second follower are operatively engaged with a distal end portion of the support member, wherein the first follower comprises a first follower outer surface and the second follower comprises a second follower outer surface, and wherein the first follower outer surface and the second follower outer surface are positioned to define a first longitudinal follower axis and a second longitudinal follower axis, respectively, and wherein the first longitudinal follower axis and the second longitudinal follower axis intersect the longitudinal slot axis;

receiving the discrete substrate in a first position on at least a portion of the head assembly; and rotating the discrete substrate to a second position, wherein the first position is different than the second position;

wherein the first longitudinal follower axis forms an angle between about 5 and about 60 degrees with the longitudinal transfer axis.

20. A rotation apparatus for rotating a discrete article, the rotation apparatus comprising:

a slot portion defined by a mounting surface, the slot portion comprising a first slot surface, a second slot surface opposite the first slot surface, and an inner slot surface extending between the first slot surface and the second slot surface, wherein the slot portion includes a motion zone and a dwell zone, wherein the slot portion defines a longitudinal slot axis of rotation;

a transfer member positioned adjacent to the slot portion, wherein the transfer member defines a longitudinal transfer axis of rotation, and wherein the transfer member comprises a proximal end portion and a distal end portion;

a support member extending from the distal end portion of the transfer member toward the slot portion, the support member having a proximal end portion and a distal end portion opposite the proximal end portion;

a first follower and a second follower operatively engaged with the distal end portion of the support member, wherein the first follower comprises a first follower outer surface and the second follower comprises a second follower outer surface, and wherein the first follower outer surface defines a first longitudinal follower axis and the second follower outer surface define a second longitudinal follower axis, and wherein the first and second longitudinal follower axes intersects the longitudinal slot axis at the same point; and wherein the transfer member and the support member are configured to rotate about the longitudinal slot axis; and wherein the first longitudinal follower axis forms an angle between about 5 and about 60 degrees with the longitudinal transfer axis.

\* \* \* \* \*